United States Patent
Chi et al.

(10) Patent No.: US 9,553,277 B2
(45) Date of Patent: *Jan. 24, 2017

(54) IRIDIUM COMPLEXES AND ORGANIC LIGHT-EMITTING DIODES USING THE SAME

(71) Applicant: National Tsing Hua University, Hsinchu (TW)

(72) Inventors: Yun Chi, Hsinchu (TW); Chu-Yun Kuei, New Taipei (TW)

(73) Assignee: National Tsing Hua University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,634

(22) Filed: May 16, 2016

(65) Prior Publication Data

US 2016/0359129 A1 Dec. 8, 2016

Related U.S. Application Data

(63) Continuation-in-part of application No. 14/806,801, filed on Jul. 23, 2015.

(30) Foreign Application Priority Data

Jun. 5, 2015 (TW) .............................. 104118339 A

(51) Int. Cl.
| | | |
|---|---|---|
| *C07F 15/00* | (2006.01) | |
| *H01L 51/50* | (2006.01) | |
| *H01L 51/00* | (2006.01) | |
| *C09K 11/06* | (2006.01) | |

(52) U.S. Cl.
CPC ....... *H01L 51/5016* (2013.01); *C07F 15/0033* (2013.01); *C09K 11/06* (2013.01); *H01L 51/0085* (2013.01); *C09K 2211/185* (2013.01)

(58) Field of Classification Search
USPC ........................................ 546/2, 10; 313/504
See application file for complete search history.

(56) References Cited

PUBLICATIONS

Wilkinson et al., "Luminescent Complexes of Iridium(III) Containing NCN-Coordinating Terdentate Ligands," Inorganic Chemistry, Sep. 2006, pp. 8685-8699.

Chu-Yun Kuei, et al, "Bis-Tridentate Ir(III) Complexes with Nearly Unitary RGB Phosphorescence and Organic Light-Emitting Diodes with External Quantum Efficiency Exceeding 31%," Advanced Materials, Feb. 19, 2016, pp. 1 -6.

*Primary Examiner* — Charanjit Aulakh
(74) *Attorney, Agent, or Firm* — J.C. Patents

(57) ABSTRACT

An iridium complex represented by formula (1) and an OLED using the same are shown. In Formula (1), l, m, n, p, b, $R^1$-$R^6$, $X^1$-$X^6$, $A^1$, $A^2$ and B are the same as defined in the specification. The iridium complex is able to emit a range of visible light with high color purity and high efficiency as neat sample.

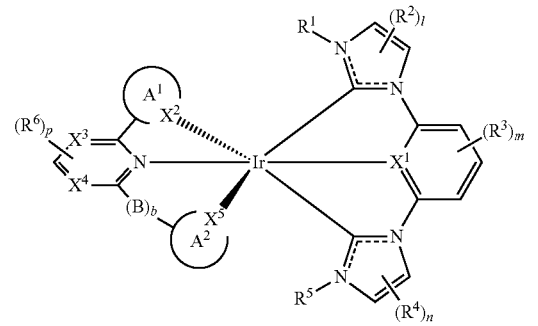

(1)

15 Claims, 2 Drawing Sheets

IRIDIUM COMPLEXES AND ORGANIC LIGHT-EMITTING DIODES USING THE SAME

CROSS-REFERENCE TO RELATED APPLICATION

This application is a continuation-in-part application of and claims the priority benefit of a prior U.S. application Ser. No. 14/806,801, filed on Jul. 23, 2015, now pending. The prior U.S. application Ser. No. 14/806,801 claims the priority benefit of Taiwan application serial no. 104118339, filed on Jun. 5, 2015. The entirety of each of the above-mentioned patent applications is hereby incorporated by reference herein and made a part of this specification.

BACKGROUND OF THE INVENTION

1. Field of the Invention

The present invention relates to the technology of organic emitting materials, and particularly to the novel phosphorescent emitters, wherein the said phosphorescent emitters belong to a class of iridium (III) based phosphor bearing a pincer carbene chelate.

2. Description of Related Art

It is well known that organic light emitting diode (OLED) device was initially invented and proposed by Eastman Kodak through a vacuum evaporation method. Tang and VanSlyke from Kodak deposited a multilayer architecture of organic semiconducting materials, such as aromatic diamine and $Alq_3$ on a transparent indium tin oxide (abbreviated as ITO) conducting glass to form the hole transporting layer (HTL), light emitting layer (EML), and subsequently completed the fabrication of an organic electroluminescent (EL) device by depositing a metal electrode on top of the $Alq_3$ layer. Thereafter, the respective EL devices become the new generation of lighting device for flat panel displays or solid state luminaires because of the high brightness, fast response time, light weight, compactness, true color, wide viewing angles, without the need for LCD backlighting plates, and low power consumption.

One important factor that controlled the luminescence efficiency of OLEDs is the light-emitting material within the emitting layer. It has been proposed that the emission is produced from the excitons derived from the recombination of electrons and holes in the light-emitting layer (material) of OLED devices. According to electron spin statistics, the ratio of the triplet excitons versus the singlet excitons is approx. 3:1 upon conducting the electric excitation. So that, when a fluorescent material is used as the light-emitting layer of OLED, only the 25% of the singlet excitons can be used to generate the luminescence, while the rest of 75% of triplet excitons are lost through the non-radiative processes. For this reason, the typical fluorescent material would produce a maximum internal quantum efficiency of 25%, which amounts to an external quantum efficiency of only 5% in the as-fabricated OLED devices.

Cyclometalated Ir(III) metal complexes, such as red emitting $Ir(btp)_2(acac)$ (i.e., bis(2-(2'-benzothienyl)-pyridinato-N,C3')iridium(acetylacetonate)), green emitting $Ir(ppy)_3$ (i.e., fac-tris(2-phenylpyridine)iridium(III)), and blue emitting Firpic (i.e., bis[2-(4,6-difluorophenyl)pyridinato-C2,N](picolinato)iridium(III)]), belong to a class of distinctive phosphorescent emitters. The chemical structures of the aforementioned $Ir(btp)_2(acac)$, $Ir(ppy)_3$ and Firpic are represented by the chemical formulas I', II' and III' showed below:

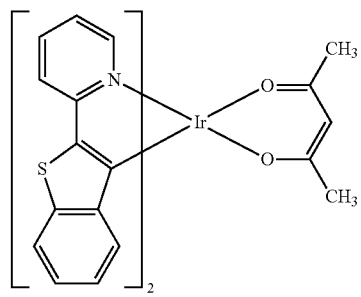

[chemical formula I']

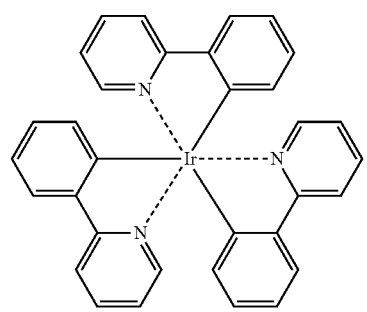

[chemical formula II']

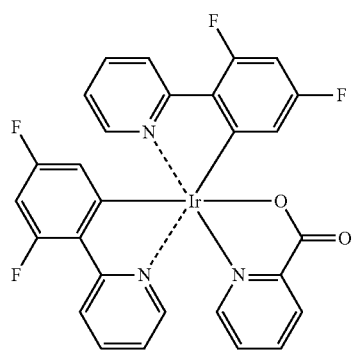

[chemical formula III']

In 2006, Andrew et al. reported a research paper entitled "Luminescent Complexes of Iridium (III) Containing N^C^N-Coordinating Tridentate Ligands", in which an iridium (III) metal complex bearing tridentate N^C^N-coordinating chelate has been proposed to be a potentially useful phosphorescent emitter for fabrication of OLEDs and associated optoelectronic devices. These Ir(III) metal complexes are named as Ir(dpyx)(dppy) and Ir(dpyx)($F_4$dppy), wherein their chemical structures are represented by following chemical formulas IV' and V', respectively.

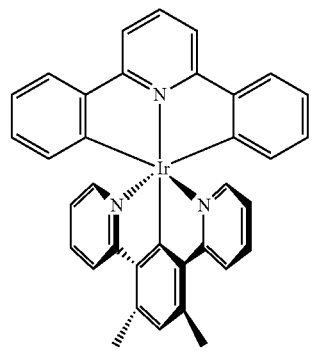

[chemical formula IV']

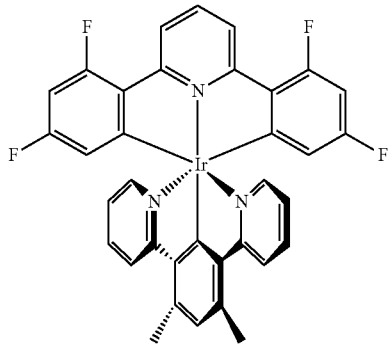

[chemical formula V']

However, these cyclometalated Ir(III) metal complexes reveal three important drawbacks when used as emitters in fabrication of OLEDs: e.g. poor luminescence efficiency, non-tunable color hue, and low synthetic yield (37% and 21%, respectively). Therefore, the person skilled in OLED art is able to assume that, these cyclometalated Ir(III) metal complexes cannot be produced in larger quantity because of the higher manufacturing cost, and cannot be served as the suitable light-emitting material due to the practical difficulty in conducting the color tuning. Moreover, since the pyridine ligand in the aforesaid cyclometalated Ir(III) metal complex linked to the central metal atom through two terminal Ir—N coordination bonds, the associated bond energy is not strong enough to induce a sufficiently large crystal field for destabilizing the metal-centered dd excited state, which usually served as the quenching state that can effectively reduce the emission quantum yield under all conditions. For this reason, the cyclometalated Ir(III) metal complex cannot afford suitable stability and luminescence efficiency.

Moreover, it is notable that, the emitters at the lowest energy excited states in an organic light-emitting material are capable to be promoted to the higher lying metal-centered dd excited state by thermal population. As a result, the excitons at the metal-centered dd excited state may possess longer emission lifetime and have higher tendency for undergoing non-radiative deactivation, resulting in a significantly reduced emission quantum yield. Such an observation is particularly notable for the typical blue or true-blue emitting phosphorescent materials.

Therefore, according to above descriptions, the person skilled in the art of OLED fabrication and material design are able to deduce that the conventional cyclometalated Ir(III) metal complexes and/or the common blue-emitting materials have the following drawbacks and shortcoming: (1) the crystal field of the iridium (III) metal complex is not strong enough to warrant a relatively higher lying metal centered dd excited state; (2) the physical stability of the iridium (III) metal complex is inadequate; (3) the non-radiative decay in the blue-emitting material cannot be effectively reduced; and (4) the quantum yield of the blue-emitting material is too low to have any practical applicability.

Accordingly, in view of the conventional cyclometalated Ir(III) metal complexes and the commercial blue-emitting materials still possess many drawbacks, the inventor of the present application has made great efforts on research thereon and eventually provided a series of iridium (III) based phosphors bearing a pincer carbene chelate, which are novel phosphorescent emitters capable of serving as excellent dopant emitters in OLEDs.

SUMMARY OF THE INVENTION

The primary objective of the present invention is to provide a series of iridium (III) based phosphor bearing a pincer carbene chelate. These novel phosphorescent Ir(III) metal complexes are capable of serving as excellent OLED emitters. Since the phosphorescent Ir(III) metal complexes proposed by the present invention possess several strong coordination bonds between ligand and metal atom (both Ir—C and Ir—N bonds), the non-radiative decay originated from the higher lying metal centered dd excited state can be effectively suppressed. Thus, this class of phosphorescent Ir(III) metal complex is capable of giving emission across the whole visible region (from blue to red) with high color purity and high luminous efficiency. Moreover, this class of novel phosphorescent Ir(III) metal complexes is also adapted for being doped in an host light-emitting layer of OLED, so as to be a guest emitter opposite to the host light-emitting layer.

Accordingly, the present invention provides an iridium complex represented by formula (1):

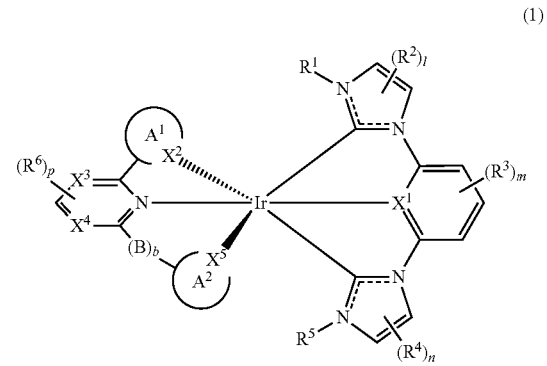

(1)

wherein each of l and n is an integer of 1 to 2; each of m and p is an integer of 1 to 3; b is an integer of 0 or 1; $R^1$ is substituted or unsubstituted $C_{1-12}$ alkyl; each of $R^2$'s is independently hydrogen or substituted or unsubstituted $C_{1-2}$ alkyl, provided that when l=2, two $R^2$'s may join to form a $C_{3-8}$ N-heteroaromatic or aromatic ring; each of $R^3$'s is independently hydrogen, fluorine or —$C_xF_{2x+1}$ (x=1, 2 or 3), substituted or unsubstituted $C_{1-2}$ alkyl, or substituted or unsubstituted $C_{6-12}$ aryl, provided that when m≥2, two or more $R^3$'s may join to form a $C_{3-8}$ aromatic ring; each of $R^4$'s is independently hydrogen or substituted or unsubstituted $C_{1-12}$ alkyl, provided that when n=2, two $R^4$'s may join to form a $C_{3-8}$ N-heteroaromatic or aromatic ring; $R^5$ is substituted or unsubstituted $C_{1-12}$ alkyl; each of $R^6$'s is independently hydrogen, fluorine or —$C_xF_{2x+1}$ (x=1, 2 or 3), substituted or unsubstituted $C_{1-12}$ alkyl, or substituted or unsubstituted $C_{6-12}$ aryl, provided that when p≥2, two or more $R^6$'s may join to form a $C_{3-8}$ N-heteroaromatic or aromatic ring; each of $X^1$, $X^2$, $X^3$, $X^4$ and $X^5$ is independently nitrogen or carbon; each of $A^1$ and $A^2$ is independently a 5-membered or 6-membered ring; and B is —O—, —$CH_2$—, —$CR_2$— or —NR— (R=methyl, ethyl or propyl), provided that when b=1.

The OLED of the invention includes two electrodes and a light-emitting layer disposed between the opposite electrodes, wherein the light-emitting layer contains the iridium complex of the invention. The iridium complex may possibly function as a dopant in a host material of the light-emitting layer.

The iridium complex of the invention has strong coordination bonding between metal center and ligand so that the transition energy to the metal-centered dd excited states is raised and the non-radiative quenching of phosphorescence is reduced, thus improving the luminous efficiency for various emission colors across the visible spectrum. In addition, the iridium complex of the invention includes a pincer carbene chelate as a strong-field ligand, which form stronger bonding with iridium so that the stability of the complex is higher.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
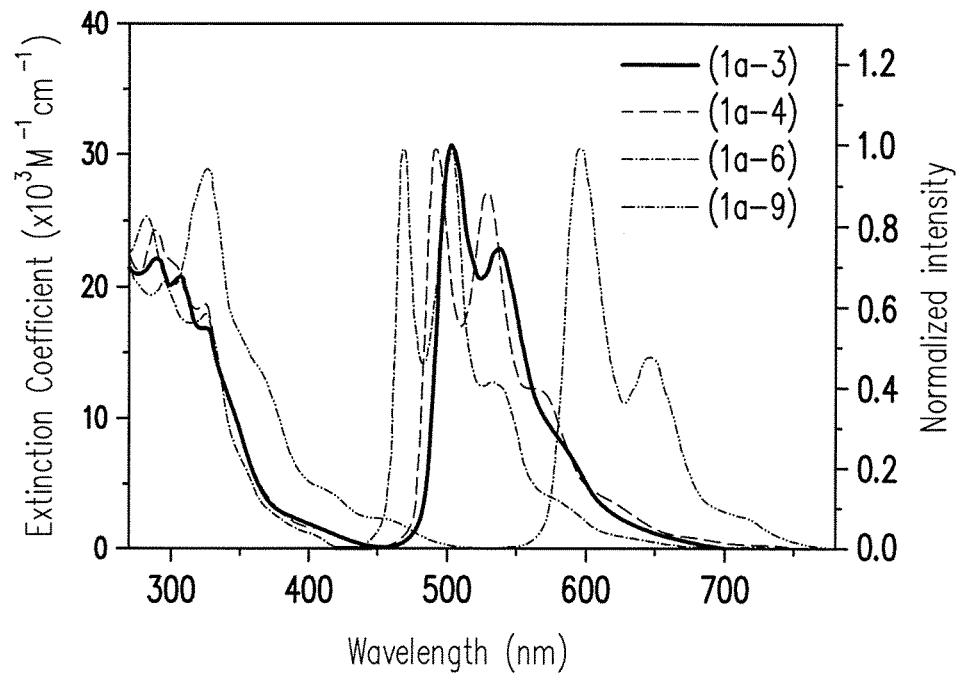
FIG. 1 shows the absorption spectra and the phosphorescence spectra of the iridium complexes (1a-3), (1a-4), (1a-6) and (1a-9) of the invention.

Reference will now be made in detail to the present preferred embodiments of the invention, examples of which are illustrated in the accompanying drawings.

Wherever possible, the same reference numbers are used in the drawings and the description to refer to the same or like parts.

To clearly describe iridium (III) metal based phosphor bearing a pincer carbene chelate according to the present invention, embodiments of the present invention will be described in detail with reference to the attached drawings hereinafter.

The iridium complex having a pincer carbene chelate of the invention is represented by formula (1):

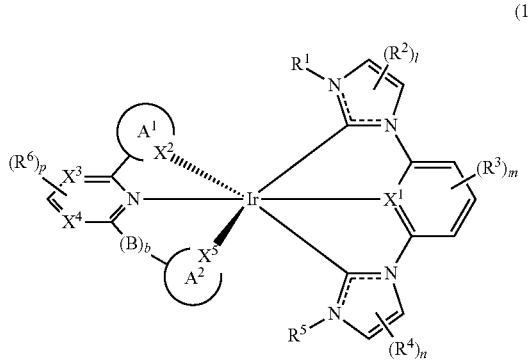

(1)

wherein each of l and n is an integer of 1 to 2; each of m and p is an integer of 1 to 3; b is an integer of 0 or 1; $R^1$ is substituted or unsubstituted $C_{1-12}$ alkyl; each of $R^2$'s is independently hydrogen or substituted or unsubstituted $C_{1-2}$ alkyl, provided that when l=2, two $R^2$'s may join to form a $C_{3-8}$ N-heteroaromatic or aromatic ring; each of $R^3$'s is independently hydrogen, fluorine or —$C_xF_{2x+1}$ (x=1, 2 or 3), substituted or unsubstituted $C_{1-12}$ alkyl, or substituted or unsubstituted $C_{6-12}$ aryl, provided that when m≥2, two or more $R^3$'s may join to form a $C_{3-8}$ aromatic ring; each of $R^4$'s is independently hydrogen or substituted or unsubstituted $C_{1-12}$ alkyl, provided that when n=2, two $R^4$'s may join to form a $C_{3-8}$ N-heteroaromatic or aromatic ring; $R^5$ is substituted or unsubstituted $C_{1-12}$ alkyl; each of $R^6$'s is independently hydrogen, fluorine or —$C_xF_{2x+1}$ (x=1, 2 or 3), substituted or unsubstituted $C_{1-12}$ alkyl, or substituted or unsubstituted $C_{6-12}$ aryl, provided that when p≥2, two or more $R^6$'s may join to form a $C_{3-8}$ N-heteroaromatic or aromatic ring; each of $X^1$, $X^2$, $X^3$, $X^4$ and $X^5$ is independently nitrogen or carbon; each of $A^1$ and $A^2$ is independently a 5-membered or 6-membered ring; and B is —O—, —$CH_2$—, —$CR_2$— or —NR— (R=methyl, ethyl or propyl), provided that when b=1.

Each of the 5-membered ring and the 6-membered ring is an aromatic hydrocarbon ring or an aromatic heterocyclic ring. Specific examples of the aromatic ring include a benzene ring, a pyridine ring, a pyrazine ring, a pyrimidine ring, a pyridazine ring, a triazine ring, a quinoline ring, an isoquinoline ring, a pyrrole ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrazole ring.

In an embodiment, the ligand at the right half of formula (1) is a tridentate pincer carbene chelate, and the ligand at the left half of formula (1) is an N^N^C tridentate chelate or a C^N^C tridentate chelate or an N^N^N tridentate chelate. The highest occupied molecular orbital (HOMO) of the iridium complex of the invention is adjusted mainly with the N^N^C, C^N^C or N^N^N tridentate chelate. The lowest unoccupied molecular orbital (LUMO) is adjusted mainly with the tridentate pincer carbene chelate.

In an embodiment, when $A^1$ is a 5-membered ring and $A^2$ is a 6-membered ring, the iridium complex is represented by formula (1a):

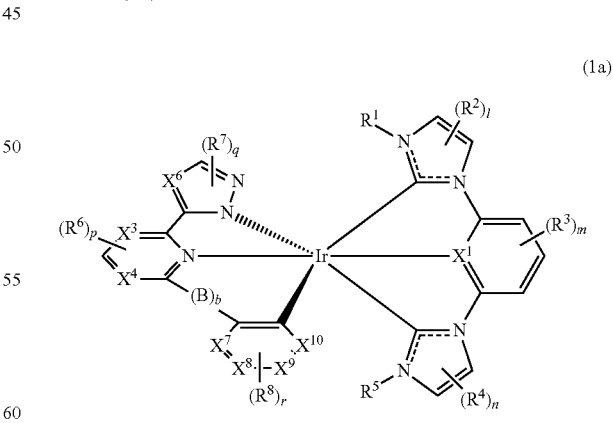

(1a)

wherein q is an integer of 1 to 2; r is an integer of 1 to 4; each of $R^7$'s is independently hydrogen, fluorinated alkyl —$C_xF_{2x+1}$ (x=1, 2 or 3) or substituted or unsubstituted $C_{1-12}$ alkyl; each of $R^8$'s is independently hydrogen, fluorinated alkyl —$C_xF_{2x+1}$ (x=1, 2 or 3) or substituted or unsubstituted $C_{1-12}$ alkyl, provided that when r≥2, two or more $R^7$'s may join to form a $C_{3-8}$ N-heteroaromatic or aromatic ring; each of $X^6$, $X^7$, $X^8$, $X^9$ and $X^{10}$ is independently nitrogen or carbon; and l, m, n, p, b, $R^1$-$R^6$, $X^1$-$X^5$, $A^1$, $A^2$ and B are as defined in formula (1).

In an embodiment, the 5-membered ring includes a nitrogen-containing aromatic heterocyclic ring such as a substituted or unsubstituted pyrazole ring. In an embodiment, the 6-membered ring includes a substituted or unsubstituted benzene ring or a nitrogen-containing aromatic heterocyclic ring such as a substituted or unsubstituted pyridine ring or a substituted or unsubstituted pyrimidine ring.

When $A^1$ is a 5-membered ring and $A^2$ is a 6-membered ring, specific examples of the iridium complexes satisfying formula (1a) include the following iridium complexes represented by formulas (1a-1), (1a-2), (1a-3), (1a-4), (1a-5), (1a-6) . . . (1a-33), respectively, abbreviated as complexes (1a-1), (1a-2), . . . hereinafter. The abbreviation rule also applies to the later described iridium complexes represented by other chemical structures.

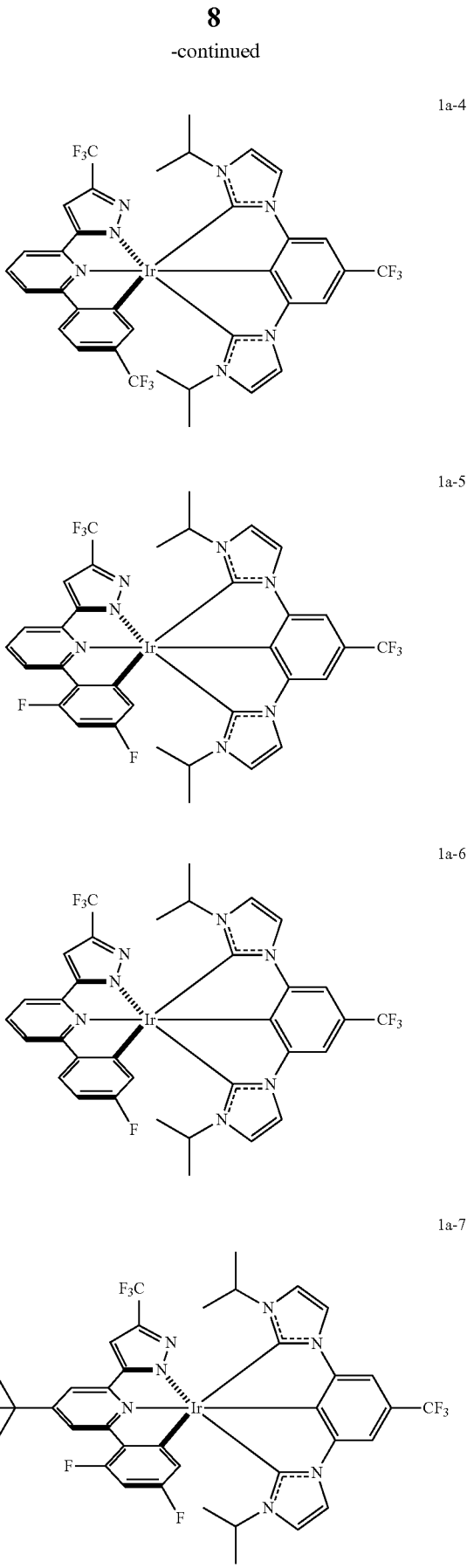

1a-8
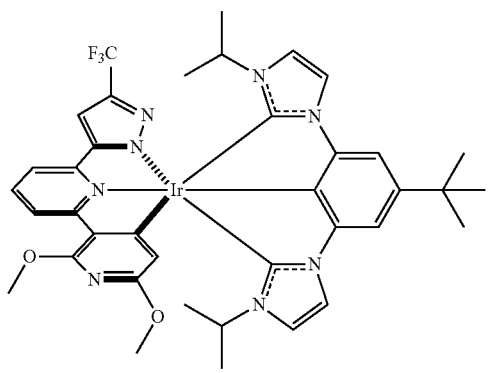
1a-9
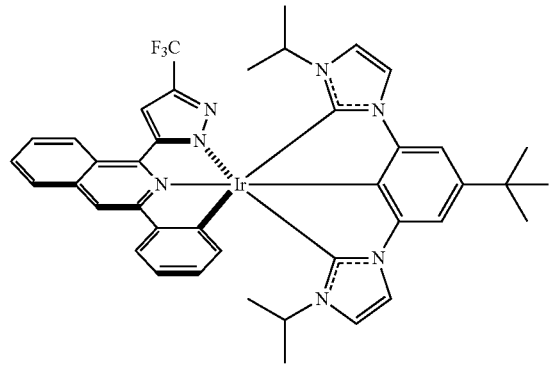
1a-10
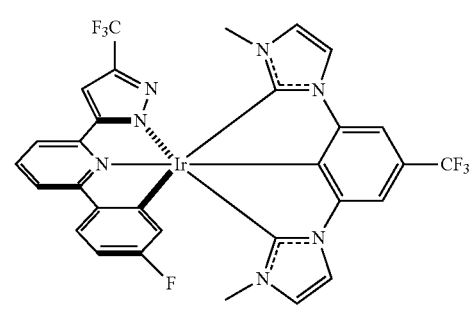
1a-11
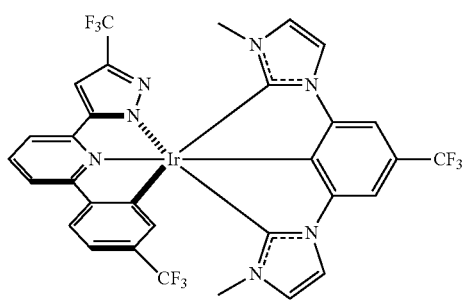
1a-12
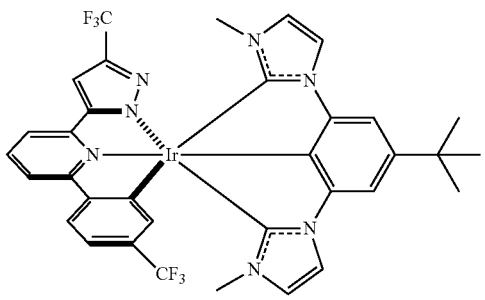
1a-13
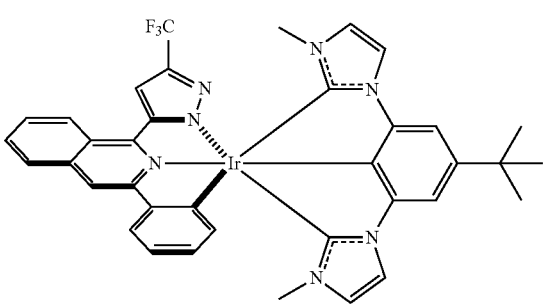
1a-14
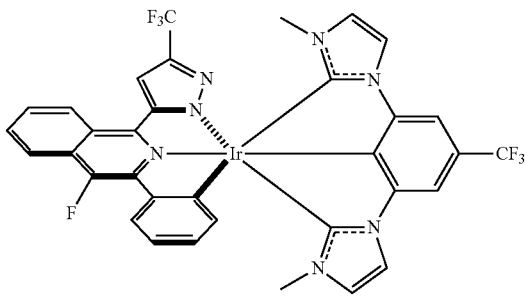
1a-15
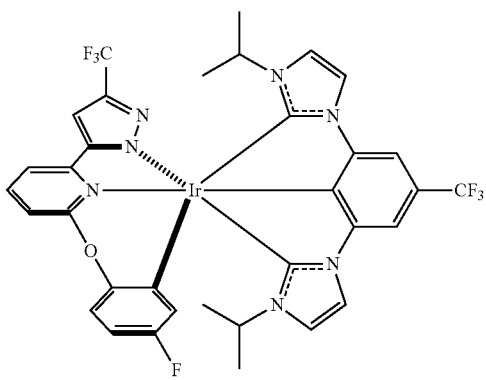

1a-16
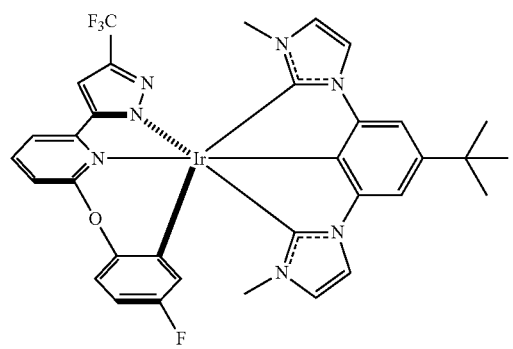
1a-17
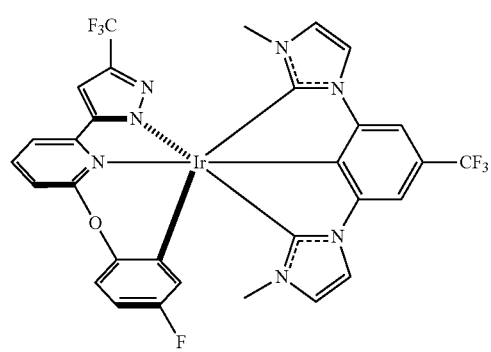
1a-18
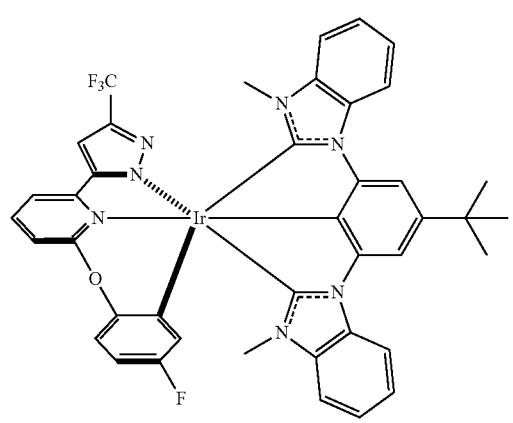
1a-19
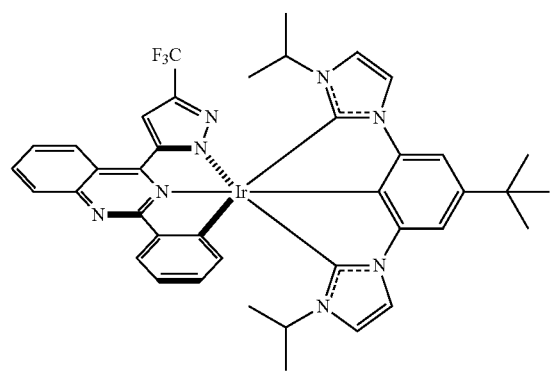
1a-20
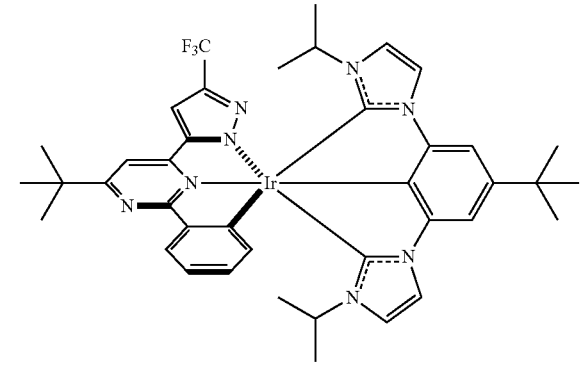
1a-21
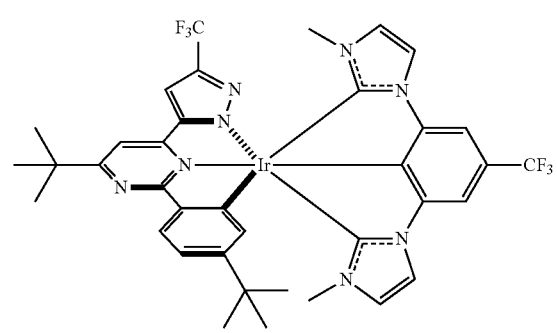
1a-22
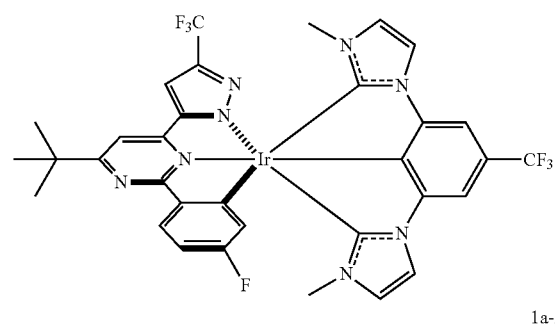
1a-23
1a-24
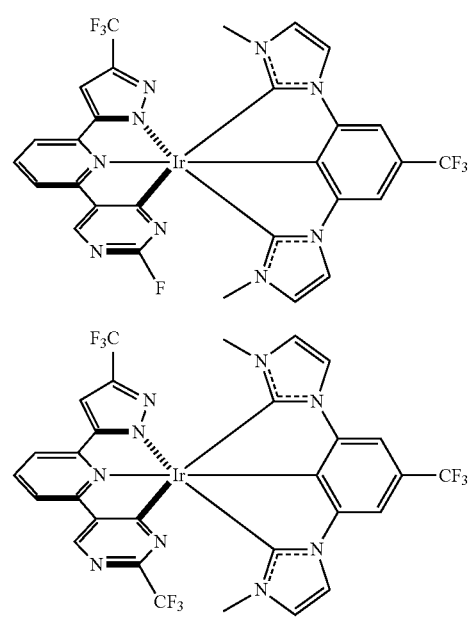

1a-25
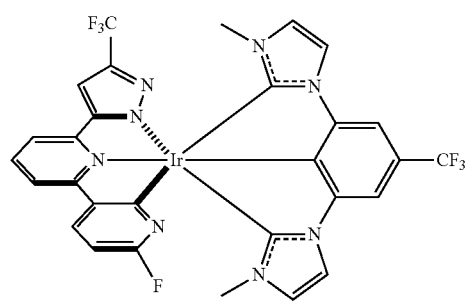

1a-26
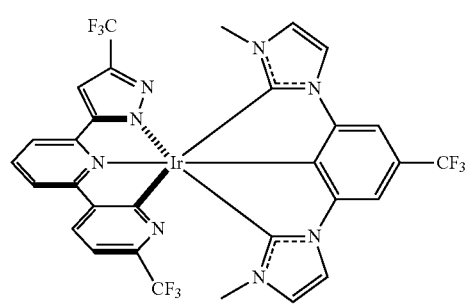

1a-27
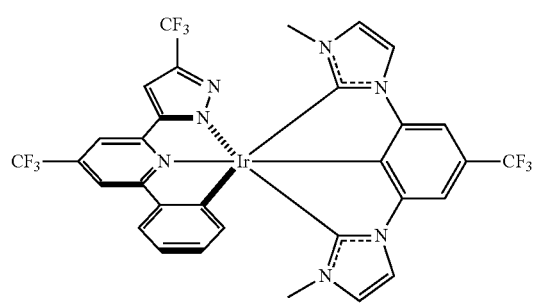

1a-28
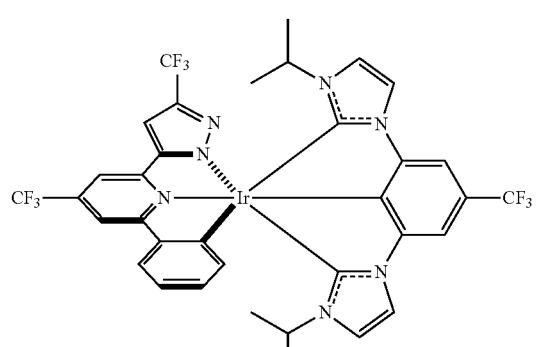

1a-29
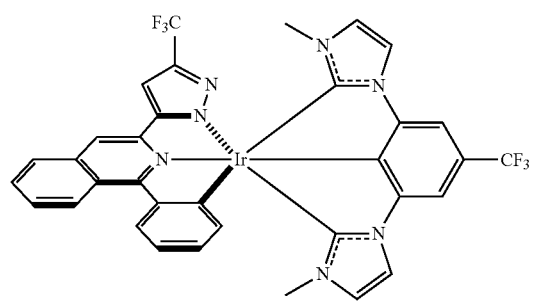

1a-30
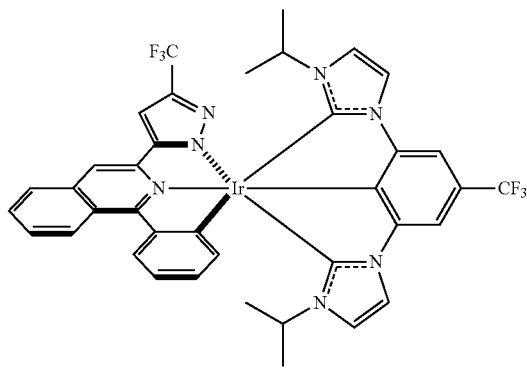

1a-31
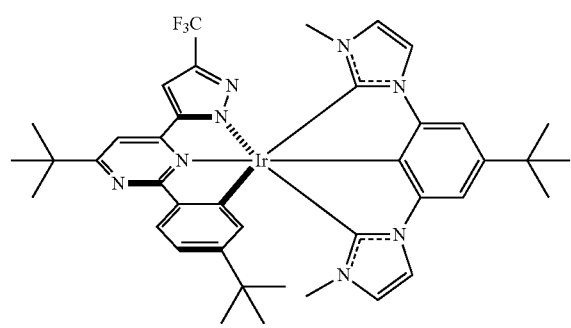

1a-32
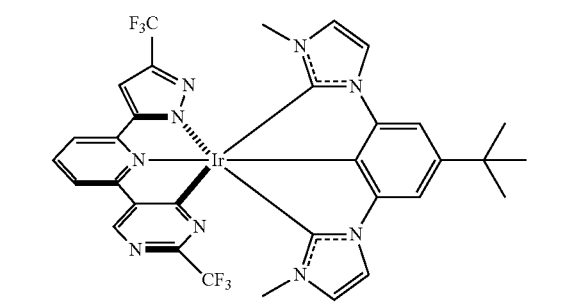

1a-33
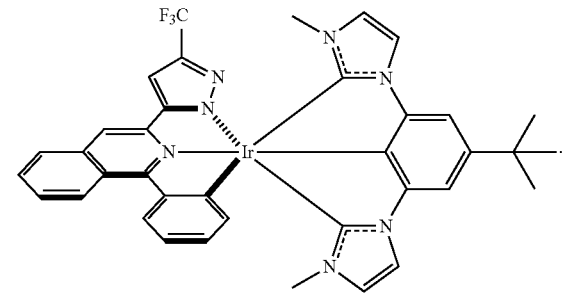

Specifically, the iridium complexes represented by formulae (1a-1) to (1a-14) are specific examples of formula (1) in which $A^1$ is a substituted or unsubstituted pyrazole ring, $A^2$ is a substituted or unsubstituted benzene ring, each of $X^1$, $X^3$, $X^4$ and $X^5$ is carbon, $X^2$ is nitrogen, and b is 0.

The iridium complexes represented by formulae (1a-15) to (1a-18) are specific examples of formula (1) in which $A^1$ is a substituted or unsubstituted pyrazole ring, $A^2$ is a substituted or unsubstituted benzene ring, each of $X^1$, $X^3$, $X^4$ and $X^5$ is carbon, $X^2$ is nitrogen, and b is 1.

The iridium complexes represented by formulae (1a-19) to (1a-22) are specific examples of formula (1) in which $A^1$ is a substituted or unsubstituted pyrazole ring, $A^2$ is a substituted or unsubstituted benzene ring, each of $X^1$ and $X^5$ is carbon, $X^2$ and at least one of $X^3$ and $X^4$ is nitrogen, and b is 0.

The iridium complexes represented by formulae (1a-23) to (1a-24) and (1a-32) are specific examples of formula (1) in which $A^1$ is a substituted or unsubstituted pyrazole ring, $A^2$ is a substituted or unsubstituted pyrimidine ring, each of $X^1$, $X^3$, $X^4$ and $X^5$ is carbon, $X^2$ is nitrogen, and b is 0.

The iridium complexes represented by formulae (1a-25) to (1a-26) are specific examples of formula (1) in which $A^1$ is a substituted or unsubstituted pyrazole ring, $A^2$ is a substituted or unsubstituted pyridine ring, each of $X^1$, $X^3$, $X^4$ and $X^5$ is carbon, $X^2$ is nitrogen, and b is 0.

The iridium complexes represented by formulae (1a-27) to (1a-31) and (1a-33) are specific examples of formula (1) in which $A^1$ is a substituted or unsubstituted pyrazole ring, $A^2$ is a substituted or unsubstituted benzene ring, each of $X^1$, $X^3$, $X^4$ and $X^5$ is carbon, $X^2$ is nitrogen, and b is 0.

In an embodiment, when $A^1$ is a 5-membered ring and $A^2$ is a 5-membered ring, the iridium complex is represented by formula (1b):

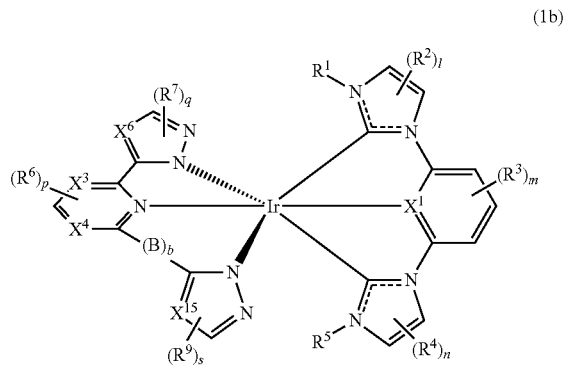

(1b)

wherein each of q and s is an integer of 1 to 2; each of $R^7$'s is independently hydrogen, fluorinated alkyl —$C_xF_{2x+1}$ (x=1, 2 or 3) or substituted or unsubstituted $C_{1-12}$ alkyl; each of $R^9$'s is independently hydrogen, fluorinated alkyl —$C_xF_{2x+1}$ (x=1, 2 or 3) or substituted or unsubstituted $C_{1-12}$ alkyl; each of $X^6$ and $X^{15}$ is nitrogen or carbon; and l, m, n, p, b, $R^1$-$R^6$, $X^1$-$X^5$, $A^1$, $A^2$ and B are as defined in formula (1).

In an embodiment, when each of $A^1$ and $A^2$ is a 5-membered ring including a nitrogen-containing aromatic heterocyclic ring such as a substituted or unsubstituted pyrazole ring, specific examples of the iridium complexes satisfying formula (1b) include the following iridium complexes represented by formulas (1b-1) and (1b-2):

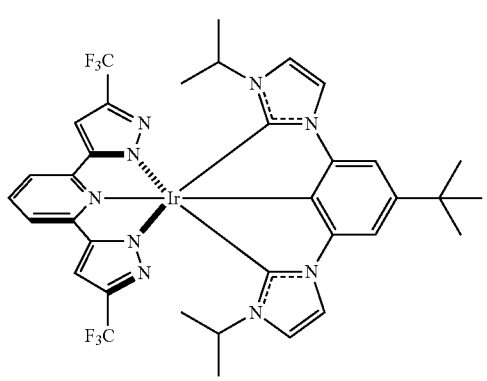

(1b-1)

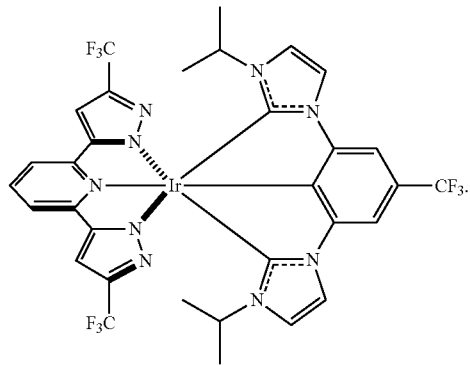

(1b-2)

In an embodiment, when $A^1$ is a 6-membered ring and $A^2$ is a 6-membered ring, the iridium complex is represented by formula (1c):

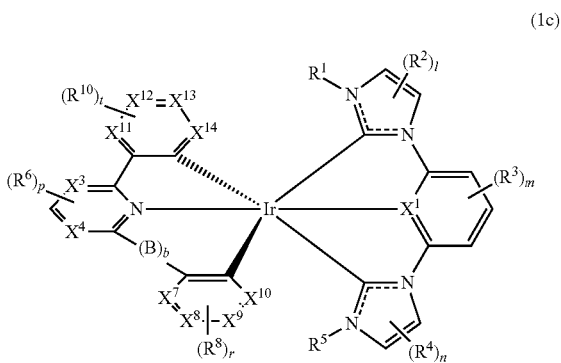

(1c)

wherein each of t and r is an integer of 1 to 4; each of $R^8$'s is independently hydrogen, fluorinated alkyl —$C_xF_{2x+1}$ (x=1, 2 or 3) or substituted or unsubstituted $C_{1-12}$ alkyl, provided that when r≥2, two or more $R^8$'s may join to form a $C_{3-8}$ aromatic ring; each of $R^{10}$'s is independently hydrogen, fluorinated alkyl —$C_xF_{2x+1}$ (x=1, 2 or 3) or substituted or unsubstituted $C_{1-12}$ alkyl, provided that when t≥2, two or more $R^{10}$'s may join to form a $C_{3-8}$ aromatic ring; each of $X^7$, $X^8$, $X^9$, $X^{10}$, $X^{11}$, $X^{12}$, $X^{13}$ and $X^{14}$ is independently nitrogen or carbon; and l, m, n, p, b, $R^1$-$R^6$, $X^1$-$X^5$, $A^1$, $A^2$ and B are as defined in formula (1).

In an embodiment, when each of $A^1$ and $A^2$ is a 6-membered ring such as a substituted or unsubstituted benzene ring, specific examples of the iridium complexes satisfying formula (1c) include the following iridium complexes represented by formulas (1c-1) and (1c-2):

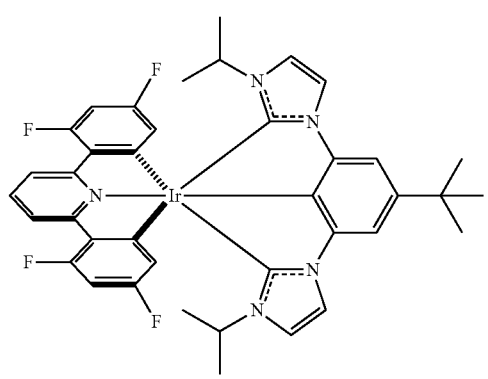

(1c-1)

-continued (1c-2)
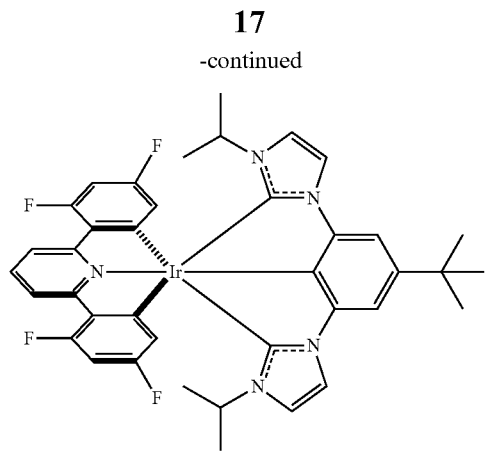

In an embodiment, the present invention provides an iridium (III) based phosphor bearing both pincer carbene and pyrazolyl chelates, which can be applied as a guest light-emitting material in the OLED applications. The said iridium (III) based phosphor bearing both pincer carbene and pyrazolyl chelates is a novel phosphorescent Ir(III) metal complex, wherein this novel phosphorescent Ir(III) metal complex is synthesized using a dicarbene chelate, a pyrazolyl-based chelate and an iridium metal source complex as starting materials under the conditions specified in the experimental section.

Inheriting to above descriptions, the novel phosphorescent Ir(III) metal complex containing both the tridentate pincer carbene and pyrazolyl chelates is represented by one of the following chemical formulas (1a-1) to (1a-9):

-continued (1a-3)
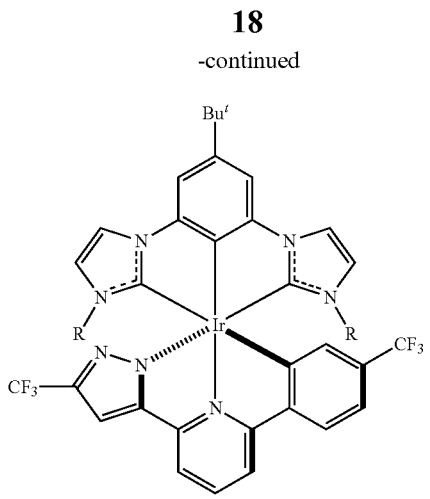

(1a-4)
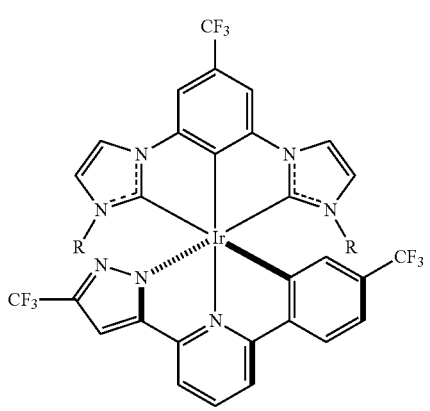

(1a-1)
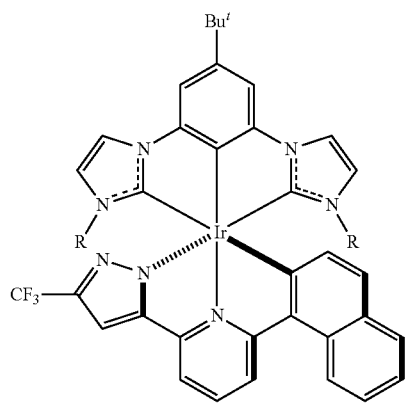

(1a-5)
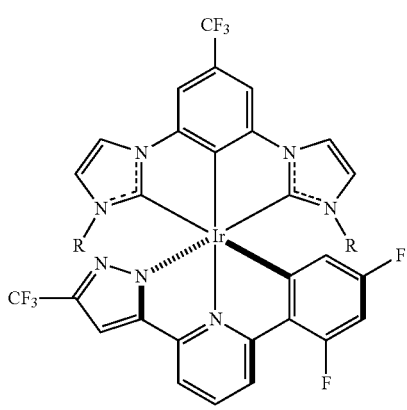

(1a-2)
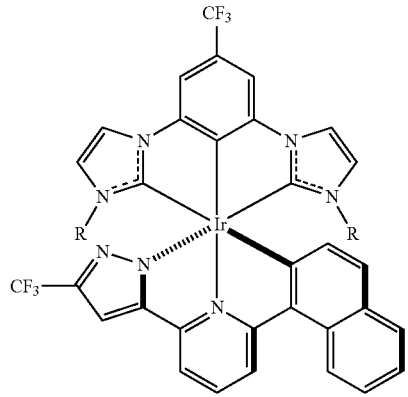

(1a-6)
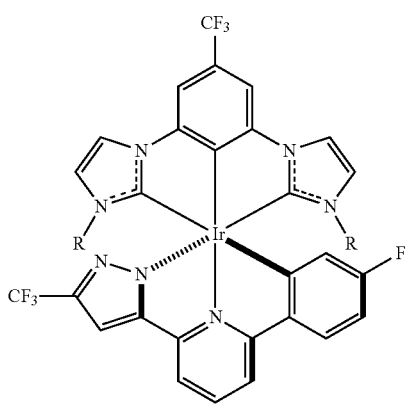

-continued

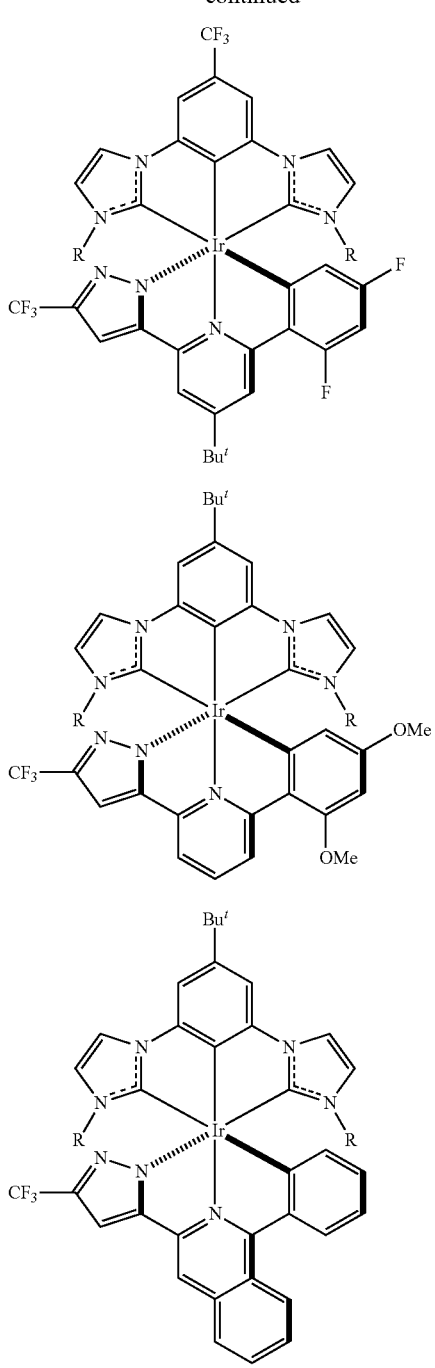

(1a-7)

(1a-8)

(1a-9)

Moreover, the synthesis for the iridium (III) based phosphor bearing both pincer carbene and pyrazolyl chelates of the present invention consists the primary steps of:

(A) preparing a dicarbene chelate through chemical synthesis;

(B) synthesis of a pyrazolyl-based chelate through chemical synthesis;

(C) obtaining an iridium metal source complex; and (D) taking the dicarbene chelate, the pyrazolyl-based chelate and the iridium metal source complex as starting materials for synthesis of the iridium (III) based phosphor bearing both pincer carbene and pyrazolyl chelate through chemical synthesis.

Continuously, a first synthetic method for the dicarbene chelate is proposed, which consists of following steps:

(S01) mixing 10 g of 1,3-dibromo-5-tert-butylbenzene (10 mmol), 1.7 g of imidazole (25 mmol), 5.5 g of $K_2CO_3$ (40 mmol), 0.08 g of $Cu_2O$ (1 mmol), and 50 mL of DMSO (dimethyl sulfoxide) so as to obtain a reaction mixture, and then stirring the mixture under 150° C. for 24 hours;

(S02) concentrating of the mixture obtained from the step (S01), so as to obtain a crude product;

(S03) preparing a silica gel column and eluting the crude product with organic solvent ($CH_2Cl_2$: MeOH=10:1, v/v) using column chromatographic technique, so as to obtain an intermediate product for the dicarbene chelate.

The intermediate product for the dicarbene chelate is represented by following chemical formula L1-1.

[chemical formula L1-1]

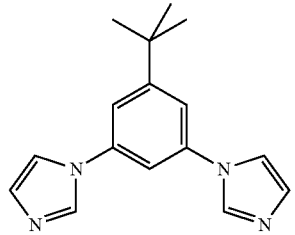

Moreover, it needs to further explain that, upon replacing 2.9 g of 1,3-dibromo-5-tert-butylbenzene (10 mmol) in the step (S01) with 3.0 g of 1,3-dibromo-5-trifluoromethylbenzene (10 mmol), the intermediate product of the following chemical formula L2-1 was obtained instead of the above-mentioned chemical formula L1-1.

[chemical formula L2-1]

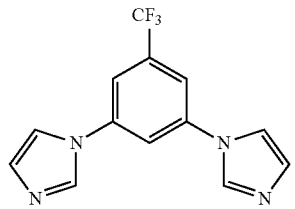

After finishing the synthesis of all intermediate products of the dicarbene chelates, a second synthetic procedure is executed for making the dicarbene chelate; wherein the second synthetic procedure consists of following steps:

(S01') adding 2.7 g of intermediate product (10 mmol) and 17 g of 2-iodopropane (100 mmol) into 30 mL of acetonitrile, and then heating the acetonitrile solution at 100° C. for 24 hours in a nitrogen-filled environment;

(S02') cooling the reaction mixture obtained from the step (S01') down to room temperature, and filtering and concentrating the solution to obtain a white solid;

(S03') dissolving the solid in 100 mL of water, and adding 16 g of ammonium hexafluorophosphate (100 mmol) into the water;

(S04') filtering and then concentrating the aqueous solution obtained from the step (S03'), so as to obtain an end product of the dicarbene chelate.

The end product of the dicarbene chelate is represented by following chemical formula L1.

[chemical formula L1]

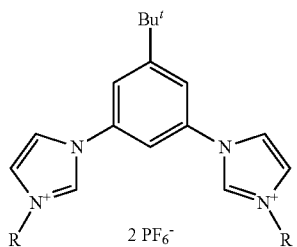

Herein, it is necessary to further explain that, upon replacing the (10 mmol, 2.7 g) intermediate product of chemical formula L1-1 in the step (S01') with (10 mmol, 2.8 g) intermediate product of chemical formula L2-1, the intermediate product for the dicarbene chelate is then represented by following chemical formula L2 instead of abovementioned chemical formula L1.

[chemical formula L2]

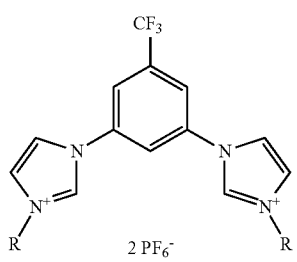

After finishing the fabrication of the dicarbene chelate, a third synthetic method for manufacturing the pyrazolyl-based chelate is continuously executed; wherein the third synthetic method consists of following steps:

(S01a) mixing the corresponding boric acid derivative with 2.0 g of 1-(6-bromopyridin-2-yl)ethanone (10 mmol), 1.4 g of $Na_2CO_3$ (10 mmol), 58 mg of $Pd(PPh_3)_4$ (0.05 mmol), and 100 mL of THF so as to obtain a mixture, and then stirring the mixture at 110° C. for 24 hours;

(S02a) concentrating the THF solution obtained from the step (S01a), so as to obtain a crude product;

(S03a) dissolving the crude product into ethyl acetate;

(S04a) filtering the solution obtained from the step (S03a) to obtain a filtrate;

(S05a) washing the filtrate with deionized water;

(S06a) removing the water in the filtrate obtained from the step (S05a) by treatment with $Na_2SO_4$, so as to obtain a crude product by concentrating the solution;

(S07a) preparing a silica gel column and eluting the crude product with a mixed organic solvent (ethyl acetate: hexane=1:5, v/v) using column chromatography, so as to obtain an intermediate product for the pyrazolyl-based chelate.

Herein, it needs to note that, the intermediate product for the pyrazolyl-based chelate would be different according to the selected boric acid derivative; therefore, these intermediate products for the pyrazolyl-based chelates are represented by the following chemical formulas L3-1, L4-1, L5-1, L6-1, L7-1, L8-1, L9-1, or L10-1.

[chemical formula L3-1]

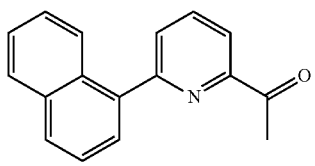

[chemical formula L4-1]

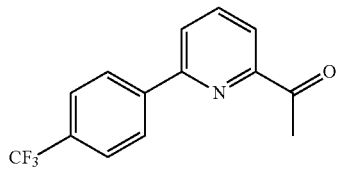

[chemical formula L5-1]

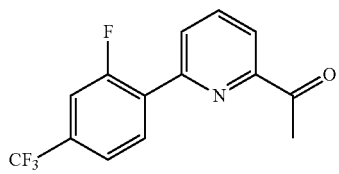

[chemical formula L6-1]

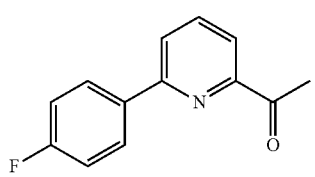

[chemical formula L7-1]

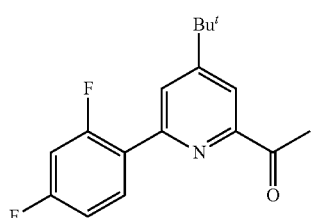

[chemical formula L8-1]

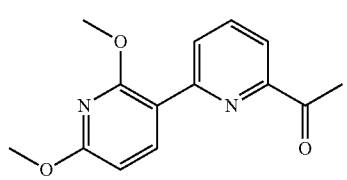

[chemical formula L9-1]

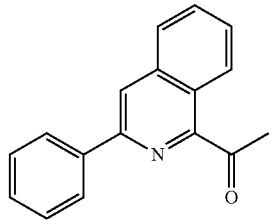

[chemical formula L10-1]

Herein, it is important to note that, although the synthetic method for L9-1 is different from the method demanded for L3-1-L8-1, the technical engineers skilled in the art of organic synthesis should be able to find a proper method for synthesizing L9-1 by way of the synthetic method of L3-1-

L8-1, based on their own experience. For above reasons, the inventor of the present invention does not elaborate how to fabricate L9-1 and L10-1 anymore.

After obtaining intermediate product for the pyrazolyl-based chelate, a fourth synthetic method for manufacturing the pyrazolyl-based chelate is subsequently proposed; wherein the fourth synthetic method consists of following steps:

(S01a') dissolving corresponding intermediate product (i.e., L3-1, L4-1, L5-1, L6-1, L7-1, L8-1, L9-1 or L10-1) of the pyrazolyl-based chelate and 0.7 g of sodium ethoxide (NaOEt, 10 mmol) into THF;

(S02a') dropping 1.4 mL of ethyl trifluoroacetate (10 mmol) into the mixture obtained from the step (S01a');

(S03a') stirring the mixture obtained from the step (S02a') at 0° C. for 12 hours;

(S04a') adding 2N HCl into the product obtained from the step (S03a'), so as to modulate the pH value of the mixture between 5 and 6;

(S05a') extracting the mixture obtained from the step (S04a') three times using ethyl acetate as extracting solvent;

(S06a') washing the extracted mixture obtained from the step (S05a') by deionized water;

(S07a') removing the water in the solution obtained from the step (S06a) by $Na_2SO_4$, so as to obtain an anhydrous solution;

(S08a') concentrating the solution obtained from the step (S07a'), and then obtaining a crude product of 1,3-dione derivative;

(S09a') dissolving the crude product of 1,3-dione derivative in 50 mL of ethanol;

(S10a') adding 5 mL of hydrazine monohydrate (100 mmol) into the solution obtained from the step (S09a'), and then heating the solution under reflux for 24 hours;

(S11a') cooling the solution obtained from the step (S10a') down room temperature;

(S12a') dissolving the crude product obtained from the step (S011a') into ethyl acetate;

(S13a') washing the ethyl acetate solution obtained from the step (S13a') by deionized water;

(S14a') drying the solution obtained from the step (S13a') by $Na_2SO_4$, followed by concentrating the solution to dryness so as to obtain a crude product;

(S15a') preparing a silica gel column and eluting the crude product by a mixed organic solvent (ethyl acetate:hexane=1:3, v/v) using column chromatography, so as to obtain an end product for the pyrazolyl-based chelate.

The end product for the pyrazolyl-based chelate is represented by following chemical formulas L3, L4, L5, L6, L7, L8, L9 or L10.

[chemical formula L3]

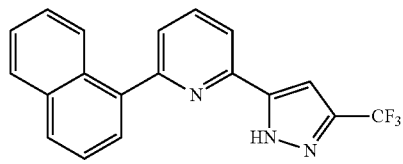

[chemical formula L4]

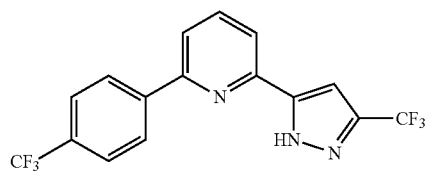

[chemical formula L5]

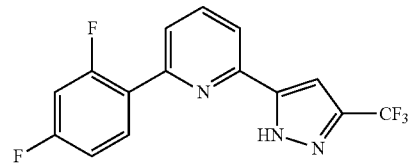

[chemical formula L6]

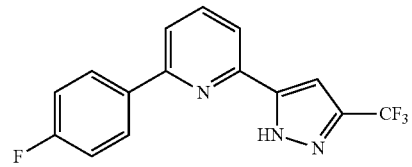

[chemical formula L7]

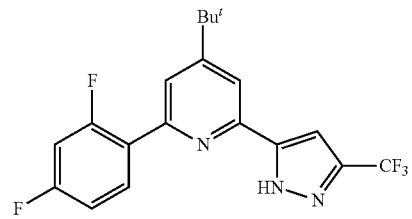

[chemical formula L8]

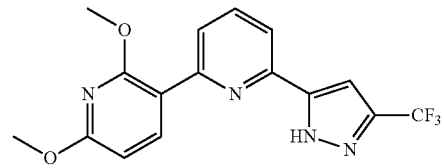

[chemical formula L9]

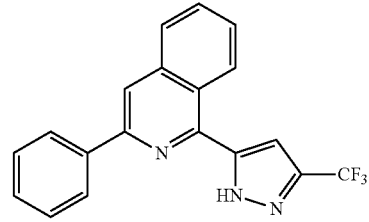

[chemical formula L10]

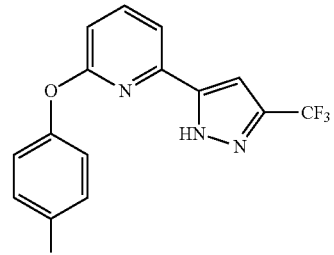

Continuously, a fifth method for synthesizing the novel phosphorescent Ir(III) metal complex containing double tridentate ligands, wherein the fifth method consists of the following steps:

(S01b) adding the dicarbene chelate of L1 or L2, the iridium metal source complex, and 336 mg of sodium acetate (NaOAc, 4 mmol) into 100 mL of acetonitrile ($CH_3CN$); wherein the said iridium metal source complex is μ-chloro-bis[1,5-cyclooctadiene] iridium (III) dimer with the molecular formula of $[Ir(COD)(\mu-Cl)]_2$;

(S02b) heating the mixture obtained from the step (S01b) at 100° C. for 12 hours under a nitrogen atmosphere;

(S03b) removing the volatile solvent of the mixture obtained from the step (S02b);

(S04b) adding corresponding pyrazolyl-based chelate (i.e., L3, L4, L5, L6, L7, L8, L9, or L10) and 100 mL of xylene into the reaction mixture obtained from the step (S03b);

(S05b) heating the mixture obtained from the step (S04b) at 140° C. for 12 hours;

(S06b) cooling the product mixture obtained from the step (S05b) down to room temperature; after then, the solvent in the product mixture is completely removed, such that a crude product for the novel phosphorescent Ir(III) metal complex is obtained;

(S07b) preparing a silica gel column and eluting the crude product with a mixed organic solvent (ethyl acetate: hexane=1:3, v/v) using chromatography technique, so as to obtain the purified product of the novel phosphorescent Ir(III) metal complex.

The related photophyscial data of the phosphorescent Ir(III) metal complex containing double tridentate ligands are recorded and compiled in Table 1. In this table, the abbreviation abs $\lambda_{max}$ stands for the absorption peak wavelength of an ultraviolet-visible absorption spectrum, while PL $\lambda_{max}$ exhibits the emission peak wavelength recorded in the photoluminescence spectrum. In addition, the Greek letters τ and Φ indicate the emission lifetime and quantum yield of the phosphorescent Ir(III) metal complex containing the double tridentate ligands. Therefore, from Table 1, it is able to know that both complexes of formulae (1a-5) and (1a-6) are the excellent emissive materials suitable for fabrication of blue phosphorescent organic light emitting diodes with high luminescence efficiency.

TABLE 1

| Ir(III) metal complex | abs $\lambda_{max}$ (nm) | PL $\lambda_{max}$ (nm) | τ (μS) | Φ (%) |
|---|---|---|---|---|
| Complex of formula (1a-1) | 282, 314, 416, 465 | 622 | 5.91 | 13 |
| Complex of formula (1a-2) | 293, 331, 428, 453 | 623 | 7.69 | 11 |
| Complex of formula (1a-3) | 289, 307, 326, 493 | 503, 537, 583, 638 | 3.04 | 98 |
| Complex of formula (1a-4) | 290, 325, 408, 486 | 492, 529, 568, 622 | 4.39 | 80 |
| Complex of formula (1a-5) | 296, 323, 406, 456 | 464, 495, 529, 577 | 4.52 | 90 |
| Complex of formula (1a-6) | 281, 326, 408, 435 | 468, 503, 533, 585 | 6.69 | 86 |
| Complex of formula (1a-7) | 277, 324, 398, 440 | 464, 496, 528, 582 | 4.67 | 75 |
| Complex of formula (1a-8) | 305, 371 | 465, 494, 526, 577 | 6.21 | 57. |
| Complex of formula (1a-9) | 326, 367, 416, 457 | 595, 647, 709 | 6.88 | 98 |

The absorption spectra and the phosphorescence spectra of the iridium complexes (1a-3), (1a-4), (1a-6) and (1a-9) are shown in FIG. 1. It is clear from FIG. 1 and Table 1 that the iridium complexes (1a-3), (1a-4), (1a-6) and (1a-9) have high quantum yields, and the iridium complex (1a-9) in which the left tridentate chelate N^N^C further includes a benzo-ring can enhance conjugation of the chromophore to reduce the energy gap and make a red shift of the emitted light.

Furthermore, the energy level of HOMO and gap of HOMO/LUMO orbital, i.e. $E_{HOMO}$ and $E_{gap}$, for these phosphorescent Ir(III) metal complex are also recorded and compiled in Table 2.

TABLE 2

| Ir(III) metal complex | $E_{HOMO}$ (eV) | $E_{gap}$ (eV) |
|---|---|---|
| Complex of formula (1a-1) | 5.17, 5.49 | 2.32 |
| Complex of formula (1a-2) | 5.33, 5.63 | 2.32 |
| Complex of formula (1a-3) | 5.23, 5.57 | 2.60 |
| Complex of formula (1a-4) | 5.51, 5.87 | 2.63 |
| Complex of formula (1a-5) | 5.53, 5.90 | 2.79 |
| Complex of formula (1a-6) | 5.48, 5.83 | 2.76 |
| Complex of formula (1a-7) | 5.48 | 2.81 |
| Complex of formula (1a-8) | 5.26, 5.55 | 2.82 |
| Complex of formula (1a-9) | 5.16 | 2.19 |

From complexes of formulae (1a-1) and (1a-9) in Table 1 and Table 2, it is able to find that, the luminescence color of the iridium (III) based phosphor bearing both pincer carbene and pyrazolyl chelates proposed by the present invention can be modulated by proper adjustment of their associated energy levels, i.e. $E_{HOMO}$ and $E_{gap}$, and molecular structure. For example, the complex of formula (1a-3) is fabricated by using the dicarbene chelate of chemical formula L1, the pyrazolyl-based chelate of chemical formula L4 as the starting materials. Besides, the complex of formula (1a-4) is fabricated by using the dicarbene chelate of chemical formula L2, the pyrazolyl-based chelate of chemical formula L4 as the starting materials. As showed in Table 1, the photoluminescence peak wavelengths of the complexes of formulae (1a-3) and (1a-4) are recorded to be 503 nm and 492 nm, respectively. That is, the phosphorescent emission of the complex of formula (1a-3) is red-shifted (i.e. with a slightly lower energy) compared to that of the complex of formula of (1a-4) under the same condition.

Accordingly, the person skilled in the art of optoelectronic material can easily understand that the $E_{HOMO}$ level (highest occupied molecular orbital energy level of host, HOMO) of the complex of formula (1a-4) is decreased by the electron-withdrawing group of $CF_3$, and that is the reason why the energy gap ($E_{gap}$) of the complex of formula (1a-4) is greater than that of the complex of formula (1a-3). Therefore, the emission peak wavelength of the complex of formula (1a-4) is found to be more blue-shifted compared with that of the complex of formula (1a-3).

Of course, among this class of proposed phosphorescent Ir(III) metal complex containing double tridentate ligands, the demanded variation of luminescence color (molecular energy level) can be modulated by variation of the pyrazolyl-based chelate. For instance, the complex of formula (1a-4) is fabricated by using the dicarbene chelate of chemical formula L2 and the pyrazolyl-based chelate of chemical formula L4 as the starting materials. Besides, the complex of formula (1a-5) is fabricated by using the dicarbene chelate of chemical formula L2 and the pyrazolyl-based chelate of chemical formula L5 as the starting materials. Moreover, as showed in Table 1, the first emission peak wavelength of the complexes of formulae (1a-4) and (1a-5) are located at 492 nm and 464 nm, respectively. That is, the complex of formula (1a-4) has a lower emission energy gap versus the complex of formula (1a-5), while its phosphorescence is more red-shifted compared to that of the complex of formula (1a-5).

It is well known that the electronegativity of fluoro group is higher than others functional group. As a result, the person skilled in the art of molecular material can easily understand that the $E_{HOMO}$ level of the complex of formula (1a-5) is lowered by the high electronegativity provided by the two fluoro groups. Hence, this explains the greater energy gap ($E_{gap}$) of the complex of formula (1a-5) versus that of the complex of formula (1a-4). Therefore, the complex of formula (1a-5) possesses larger energy gap versus the complex of formula (1a-4), and the emission color is further blue-shifted as recorded.

Through abovementioned discussion and step-by-step delineation of their optoelectronic behaviors, the systematic variation of iridium (III) based phosphor bearing both pincer carbene and pyrazolyl chelates proposed by the present invention have been clearly explained; in summary, the present invention includes the following advantages:

(1) Differing from the conventional cyclometalated Ir(III) metal complexes, this class of novel phosphorescent Ir(III) metal complex is synthesized from a class of pincer carbene derivative, a class of pyrazolyl-based chelate and an iridium metal source complex. Because the phosphorescent Ir(III) metal complex proposed by the present invention includes several strong coordination bonds (Ir—C bond), the non-radiative decay from the higher lying triplet excited state can be effectively suppressed. Thus, this novel class of phosphorescent Ir(III) metal complex is able to emit a range of visible light (particularly the blue light) with high color purity and high efficiency as neat sample. Moreover, this novel phosphorescent Ir(III) metal complex is also capable to adapt as a guest emitter in the light emitting layer (EML) for the traditional doped OLED architecture.

(2) Moreover, the experimental data of the complexes of formulae (1a-1) to (1a-9) have proved that, through proper selection of dicarbene chelate and/or pyrazolyl-based chelate, the luminescence color of the iridium (III) based phosphor bearing both pincer carbene and pyrazolyl chelates proposed by the present invention can be modulated by adjusting the corresponding energy level of HOMO and HOMO/LUMO energy gaps.

In addition to the preparation method described above, another preparation method is provided below to further describe the invention, which are merely exemplary and are not intended to limit the scope of the invention.

Examples 1-9

Preparation of Complexes (1a-1) to (1a-9)

The functional bis(imidazolium) benzene chelate (1.0 mmol), [Ir(cod)(μ-Cl)]$_2$ (0.5 mmol) and NaOAc (5.0 mmol) were added in CH$_3$CN (80 mL) and the mixture was heated and refluxed for 12 h. After removal of acetonitrile, the 2-pyrazolyl-6-phenyl pyridine class of chelate (1.0 mmol) and xylene (80 mL) were added, and the mixture was heated and refluxed at 150° C. for another 12 h. The solvent was evaporated and the residue was purified by silica gel column chromatography, eluted with ethyl acetate and hexane (1:3) to obtain the bis-tridentate Ir(III) complexes.

Data of the complex (1a-1): orange solid; yield: 44%; $^1$H NMR (400 MHz, CDCl$_3$): δ 8.60 (d, J=8.8 Hz, 1H), 8.36 (d, J=8.4 Hz, 1H), 7.84 (t, J=7.6 Hz, 1H), 7.64 (d, J=7.6 Hz, 1H), 7.58 (d, J=8.4 Hz, 1H), 7.49 (d, J=2.0 Hz, 2H), 7.44 (t, J=8.4 Hz, 1H), 7.27 (s, 2H), 7.25 (s, 1H), 6.94~6.92 (m, 2H), 6.58 (d, J=2.0 Hz, 2H), 6.12 (d, J=8.4 Hz, 1H), 3.27~3.17 (m, 2H), 1.52 (s, 9H), 0.71 (d, J=6.8 Hz, 6H), 0.63 (d, J=6.8 Hz, 6H). $^{19}$F NMR (376 MHz, CDCl$_3$): δ −59.65 (s, 3F). FAB MS: m/z 879.6 (M$^+$). Anal. Calcd. for C$_{41}$H$_{39}$F$_3$IrN$_7$: C, 56.02; H, 4.47; N, 11.15. Found: C, 55.78; H, 4.63; N, 11.24.

Data of the complex (1a-2): orange solid; yield: 60%; $^1$H NMR (400 MHz, CDCl$_3$): δ 8.59 (d, J=8.8 Hz, 1H), 8.37 (d, J=8.0 Hz, 1H), 7.89 (t, J=8.4 Hz, 1H), 7.65 (d, J=8.0 Hz, 1H), 7.59 (d, J=8.0 Hz, 1H), 7.51~7.43 (m, 4H), 7.26 (t, J=6.8 Hz, 1H), 6.95~6.92 (m, 2H), 6.64 (s, 2H), 5.96 (d, J=8.4 Hz, 1H), 5.28 (s, 1H), 3.33~3.23 (m, 2H), 0.73 (d, J=4.4 Hz, 6H), 0.66 (d, J=4.4 Hz, 6H). $^{19}$F NMR (376 MHz, CDCl$_3$): δ −59.78 (s, 3F), −60.07 (s, 3F). FAB MS: m/z 891.9 (M$^+$). Anal. Calcd. for C$_{38}$H$_{30}$F$_6$IrN$_7$: C, 51.23; H, 3.39; N, 11.01. Found: C, 51.01; H, 3.42; N, 10.86.

Data of the complex (1a-3): yellow solid; yield: 64%; $^1$H NMR (400 MHz, CDCl$_3$): δ 7.82 (t, J=8.0 Hz, 1H), 7.73 (d, J=8.0 Hz, 1H), 7.66 (d, J=8.0 Hz, 1H), 7.61 (d, J=8.0 Hz, 1H), 7.51 (d, J=2.4 Hz, 2H), 7.26 (s, 2H), 6.95 (dd, J=8.0, 1.6 Hz, 1H), 6.91 (s, 1H), 6.62 (d, J=2.4 Hz, 2H), 6.01 (s, 1H), 3.22~3.12 (m, 2H), 1.50 (s, 9H), 0.69 (d, J=6.8 Hz, 6H), 0.68 (d, J=6.8 Hz, 6H). $^{19}$F NMR (376 MHz, CDCl$_3$): δ −59.93 (s, 3F), −62.74 (s, 3F). FAB MS: m/z 898.0 (M+H$^+$). Anal. Calcd. for C$_{38}$H$_{36}$F$_6$IrN$_7$: C, 50.88; H, 4.05; N, 10.93. Found: C, 50.57; H, 4.29; N, 10.67.

Data of the complex (1a-4): yellow solid; yield: 75%; $^1$H NMR (400 MHz, CDCl$_3$): δ 7.87 (t, J=8.0 Hz, 1H), 7.76 (d, J=8.0 Hz, 1H), 7.69 (d, J=8.0 Hz, 1H), 7.64 (d, J=8.0 Hz, 1H), 7.54 (d, J=2.4 Hz, 2H), 7.46 (s, 2H), 6.99 (d, J=8.0 Hz, 1H), 6.92 (s, 1H), 6.69 (d, J=2.4 Hz, 2H), 5.91 (s, 1H), 3.27~3.16 (m, 2H), 0.73 (d, J=6.8 Hz, 6H), 0.72 (d, J=6.8 Hz, 6H). $^{19}$F NMR (376 MHz, CDCl$_3$): δ −59.98 (s, 3F), −60.24 (s, 3F), −62.78 (s, 3F). FAB MS: m/z 909.7 (M$^+$). Anal. Calcd. for C$_{35}$H$_{27}$F$_9$IrN$_7$: C, 46.25; H, 2.99; N, 10.79. Found: C, 46.08; H, 3.10; N, 10.62.

Data of the complex (1a-5): yellow solid; yield: 17%; $^1$H NMR (400 MHz, acetone-d$_6$): δ 8.19 (d, J=2.4 Hz, 2H), 8.14 (dd, J=8.0, 1.6 Hz, 1H), 8.10 (t, J=8.0 Hz, 1H), 7.99 (dd, J=8.0, 1.6 Hz, 1H), 7.85 (s, 2H), 7.25 (d, J=2.4 Hz, 2H), 7.07 (s, 1H), 6.45~6.39 (m, 1H), 5.33 (dd, J=8.8, 2.4 Hz, 1H), 3.40~3.29 (m, 2H), 0.86 (d, J=6.8 Hz, 6H), 0.80 (d, J=6.8 Hz, 6H). $^{19}$F NMR (376 MHz, acetone-d$_6$): δ −60.36 (s, 3F), −60.40 (s, 3F), −110.78 (d, J=9.4 Hz, 1F), −112.09 (d, J=9.4 Hz, 1F). FAB MS: m/z 878.2 (M+H$^+$). Anal. Calcd. for C$_{34}$H$_{26}$F$_8$IrN$_7$: C, 46.57; H, 2.99; N, 11.18. Found: C, 46.36; H, 3.21; N, 11.02.

Data of the complex (1a-6): yellow solid; yield: 52%; $^1$H NMR (400 MHz, CDCl$_3$): δ 7.81 (t, J=8.0 Hz, 1H), 7.62 (t, J=8.0 Hz, 2H), 7.57~7.55 (m, 1H), 7.53 (d, J=2.4 Hz, 2H), 7.44 (s, 2H), 6.90 (s, 1H), 6.69 (d, J=2.4 Hz, 2H), 6.46 (td, J=8.0, 2.4 Hz, 1H), 5.35 (dd, J=9.6, 2.4 Hz, 1H), 3.30~3.22 (m, 2H), 0.74 (d, J=6.8 Hz, 6H), 0.73 (d, J=6.8 Hz, 6H). $^{19}$F NMR (376 MHz, CDCl$_3$): δ −59.90 (s, 3F), −60.15 (s, 3F), −110.76 (s, 1F). FAB MS: m/z 860.2 (M+H$^+$). Anal. Calcd. for C$_{34}$H$_{27}$F$_7$IrN$_7$: C, 47.55; H, 3.17; N, 15.48. Found: C, 47.27; H, 3.31; N, 15.24.

Data of the complex (1a-7): yellow solid; yield: 22%; $^1$H NMR (400 MHz, CDCl$_3$): δ 8.12 (s, 1H), 7.68 (s, 1H), 7.55 (s, 2H), 7.45 (s, 2H), 6.95 (s, 1H), 6.72~6.70 (m, 2H), 6.26 (t, J=9.6 Hz, 1H), 5.17 (d, J=6.4 Hz, 1H), 3.24~3.15 (m, 2H), 1.53 (s, 9H), 0.78 (d, J=6.8 Hz, 6H), 0.74 (d, J=6.8 Hz, 6H). $^{19}$F NMR (376 MHz, CDCl$_3$): δ −60.35 (s, 3F), −60.39 (s, 3F), −111.22 (s, 1F), −112.43 (s, 1F). FAB MS: m/z 934.5 (M+H$^+$). Anal. Calcd. for C$_{38}$H$_{34}$F$_8$IrN$_7$: C, 48.92; H, 3.67; N, 10.51. Found: C, 48.68; H, 3.99; N, 10.27.

Data of the complex (1a-8): yellow solid; yield: 11%; $^1$H NMR (400 MHz, CDCl$_3$): δ 8.22 (d, J=8.4 Hz, 1H), 7.75 (t, J=6.4 Hz, 2H), 7.52 (d, J=7.6 Hz, 1H), 7.47 (s, 2H), 7.21 (s, 1H), 6.85 (s, 1H), 6.62 (s, 2H), 4.90 (s, 1H), 3.98 (s, 3H), 3.57 (s, 3H), 3.24~3.18 (m, 2H), 1.47 (s, 9H), 0.76 (d, J=6.8 Hz, 6H), 0.68 (d, J=6.8 Hz, 6H). $^{19}$F NMR (376 MHz, CDCl$_3$): δ −59.83 (s, 3F). FAB MS: m/z 890.8 (M$^+$). Anal. Calcd. for C$_{38}$H$_{40}$F$_3$IrN$_8$O$_2$: C, 51.28; H, 4.53; N, 12.57. Found: C, 50.99; H, 4.77; N, 12.37.

Data of the complex (1a-9): red solid; yield: 52%; $^1$H NMR (400 MHz, CDCl$_3$): δ 8.75~8.72 (m, 1H), 8.12 (s, 1H), 8.07~8.04 (m, 1H), 7.73~7.71 (m, 2H), 7.68 (d, J=7.6 Hz, 1H), 7.49 (d, J=2.0 Hz, 2H), 7.39 (s, 1H), 7.27 (s, 2H), 6.77 (td, J=8.0, 1.2 Hz, 1H), 6.58 (d, J=2.0 Hz, 2H), 6.54 (td, J=8.0, 1.2 Hz, 1H), 5.80 (d, J=7.6 Hz, 1H), 3.16~3.06 (m, 2H), 1.52 (s, 9H), 0.63 (d, J=6.8 Hz, 6H), 0.55 (d, J=6.8 Hz, 6H). $^{19}$F NMR (376 MHz, CDCl$_3$): δ −59.74 (s, 3F). FAB MS: m/z 880.1 (M+H$^+$). Anal. Calcd. for C$_{41}$H$_{39}$F$_3$IrN$_7$: C, 56.02; H, 4.47; N, 11.15. Found: C, 55.70; H, 4.25; N, 11.10.

Examples 10-13

Preparation of Complexes (1a-10) to (1a-13)

The functional bis(imidazolium) benzene chelate (1.0 mmol), [Ir(cod)(μ-Cl)]$_2$ (0.5 mmol) and NaOAc (5.0 mmol) were added in CH$_3$CN (80 mL) and the mixture was heated and refluxed for 12 h. After removal of acetonitrile, the 2-pyrazolyl-6-phenyl pyridine class of chelate (1.0 mmol) and xylene (80 mL) were added, and the mixture was heated and refluxed at 150° C. for another 12 h. The xylene was then replaced with decalin (80 mL) and the mixture was heated and refluxed for another 48 h. The solvent was evaporated and the residue was purified by silica gel column chromatography, eluted with CH$_2$Cl$_2$ and ethyl acetate (10:1) to obtain the bis-tridentate Ir(III) complexes.

Data of the complex (1a-10): yellow solid; yield: 30%; $^1$H NMR (400 MHz, acetone-d$_6$): δ 8.13 (d, J=2.0 Hz, 2H), 8.03 (t, J=8.0 Hz, 1H), 8.00 (dd, J=8.0, 1.6 Hz, 1H), 7.92 (dd, J=8.0, 1.6 Hz, 1H), 7.85 (dd, J=8.8, 5.6 Hz, 1H), 7.82 (s, 2H), 7.07 (s, 1H), 7.01 (d, J=2.0 Hz, 2H), 6.53 (td, J=8.8, 2.8 Hz, 1H), 5.40 (dd, J=8.8, 2.8 Hz, 1H), 2.90 (s, 6H). $^{19}$F NMR (376 MHz, acetone-d$_6$): δ −60.24 (s, 3F), −60.28 (s, 3F), −113.12 (s, 1F). FAB MS: m/z 803.7 (M+H$^+$). Anal. Calcd. for C$_{30}$H$_{19}$F$_7$IrN$_7$: C, 44.89; H, 2.39; N, 12.21. Found: C, 44.60; H, 2.51; N, 12.28.

Data of the complex (1a-11): yellow solid; yield: 36%; $^1$H NMR (400 MHz, acetone-d$_6$): δ 8.17 (dd, J=8.0, 0.8 Hz, 1H), 8.13 (d, J=2.0 Hz, 2H), 8.10 (t, J=8.0 Hz, 1H), 8.03 (dd, J=8.0, 0.8 Hz, 1H), 7.98 (d, J=8.0 Hz, 1H), 7.82 (s, 2H), 7.10 (s, 1H), 7.09 (d, J=8.0 Hz, 1H), 7.00 (d, J=2.0 Hz, 2H), 6.07 (s, 1H), 2.90 (s, 6H). $^{19}$F NMR (376 MHz, acetone-d$_6$): δ −60.31 (s, 3F), −60.32 (s, 3F), −63.15 (s, 3F). FAB MS: m/z 853.9 (M$^+$). Anal. Calcd. for C$_{31}$H$_{19}$F$_9$IrN$_7$: C, 43.66; H, 2.25; N, 11.50. Found: C, 43.41; H, 2.37; N, 11.51.

Data of the complex (1a-12): yellow solid; yield: 36%; $^1$H NMR (400 MHz, acetone-d$_6$): δ 8.12 (dd, J=8.0, 0.8 Hz, 1H), 8.04 (t, J=8.0 Hz, 1H), 7.98 (dd, J=8.0, 0.8 Hz, 1H), 7.97 (d, J=2.0 Hz, 2H) 7.94 (d, J=8.0 Hz, 1H), 7.61 (s, 2H), 7.08 (s, 1H), 7.04 (d, J=8.0 Hz, 1H), 6.90 (d, J=2.0 Hz, 2H), 6.17 (s, 1H), 2.83 (s, 6H), 1.51 (s, 9H). $^{19}$F NMR (376 MHz, acetone-d$_6$): δ −60.18 (s, 3F), −63.03 (s, 3F). FAB MS: m/z 842.0 (M+H$^+$). Anal. Calcd. for C$_{34}$H$_{28}$F$_6$IrN$_7$: C, 48.57; H, 3.36; N, 11.66. Found: C, 48.20; H, 3.24; N, 11.65.

Data of the complex (1a-13): orange-red solid; yield: 45%; $^1$H NMR (400 MHz, acetone-d$_6$): δ 8.95~8.92 (m, 1H), 8.49 (s, 1H), 8.24~8.20 (m, 1H), 7.96 (d, J=2.0 Hz, 2H), 7.86 (dd, J=7.6, 1.2 Hz, 1H), 7.84~7.79 (m, 2H), 7.60 (s, 2H), 7.59 (s, 1H), 6.87 (d, J=2.0 Hz, 2H), 6.77 (td, J=7.6, 1.2 Hz, 1H), 6.47 (td, J=7.6, 1.2 Hz, 1H), 5.84 (dd, J=7.6, 1.2 Hz, 1H), 2.74 (s, 6H), 1.53 (s, 9H). $^{19}$F NMR (376 MHz, acetone-d$_6$): δ −60.08 (s, 3F). FAB MS: m/z 824.2 (M+H$^+$). Anal. Calcd. for C$_{37}$H$_{31}$F$_3$IrN$_7$: C, 54.00; H, 3.80; N, 11.91. Found: C, 53.96; H, 3.85; N, 11.85.

Examples 14-16

Preparation of Complexes (1a-15) to (1a-17)

The functional bis(imidazolium) benzene chelate (1.0 mmol), [Ir(cod)(μ-Cl)]$_2$ (0.5 mmol) and NaOAc (5.0 mmol) were added in CH$_3$CN (80 mL) and the mixture was heated and refluxed for 12 h. After removal of acetonitrile, the 2-pyrazolyl-6-phenyl pyridine class of chelate (1.0 mmol) and xylene (80 mL) were added, and the mixture was heated and refluxed at 150° C. for another 12 h. The xylene was then replaced with decalin (80 mL) and the mixture was heated and refluxed for another 48 h. The solvent was evaporated and the residue was purified by silica gel column chromatography, eluted with CH$_2$Cl$_2$ to obtain the bis-tridentate Ir(III) complexes.

Data of the complex (1a-15): yellow solid; yield: 12%; $^1$H NMR (400 MHz, acetone-d$_6$): δ 8.18 (t, J=8.0 Hz, 1H), 8.16 (d, J=2.0 Hz, 2H), 7.84 (dd, J=8.0, 1.2 Hz, 1H), 7.78 (s, 2H), 7.29 (d, J=2.0 Hz, 2H), 7.23 (dd, J=8.0, 1.2 Hz, 1H), 7.00 (s, 1H), 6.84 (dd, J=8.8, 5.2 Hz, 1H), 6.31~6.26 (m, 1H), 5.46 (dd, J=10.4, 3.2 Hz, 1H), 3.74~3.67 (m, 2H), 1.04 (d, J=6.8 Hz, 6H), 0.83 (d, J=6.8 Hz, 6H). $^{19}$F NMR (376 MHz, acetone-d$_6$): δ −60.13 (s, 3F), −60.50 (s, 3F), −123.89 (s, 1F). FAB MS: m/z 875.2 (M+H$^+$).

Data of the complex (1a-16): yellow solid; yield: 15%; $^1$H NMR (400 MHz, acetone-d$_6$): δ 8.13 (t, J=7.6 Hz, 1H), 7.96 (d, J=2.0 Hz, 2H), 7.80 (dd, J=7.6, 1.2 Hz, 1H), 7.53 (s, 2H), 7.16 (dd, J=7.6, 1.2 Hz, 1H), 7.01 (s, 1H), 7.00 (d, J=2.0 Hz, 2H), 6.79 (dd, J=8.8, 5.2 Hz, 1H), 6.26~6.21 (m, 1H), 5.49 (dd, J=10.4, 3.2 Hz, 1H), 3.09 (s, 6H), 1.51 (s, 9H). $^{19}$F NMR (376 MHz, acetone-d$_6$): δ −59.94 (s, 3F), −124.09 (s, 1F). FAB MS: m/z 807.3 (M+H$^+$).

Data of the complex (1a-17): yellow solid; yield: 17%; $^1$H NMR (400 MHz, acetone-d$_6$): δ 8.18 (t, J=7.6 Hz, 1H), 8.11 (d, J=2.0 Hz, 2H), 7.84 (dd, J=7.6, 1.2 Hz, 1H), 7.76 (s, 2H), 7.23 (dd, J=7.6, 1.2 Hz, 1H), 7.09 (d, J=2.0 Hz, 2H), 7.02 (s, 1H), 6.85 (dd, J=8.8, 5.2 Hz, 1H), 6.31~6.26 (m, 1H), 5.41 (dd, J=10.4, 3.2 Hz, 1H), 3.14 (s, 6H). $^{19}$F NMR (376 MHz, acetone-d$_6$): δ −60.14 (s, 3F), −60.46 (s, 3F), −124.05 (s, 1F). FAB MS: m/z 819.2 (M+H$^+$).

Example 17

Preparation of Complex (1a-18)

The functional bis(imidazolium) benzene chelate (1.0 mmol), IrCl$_3$.3H$_2$O (1.0 mmol), 2-pyrazolyl-6-phenyl pyridine class of chelate (1.0 mmol) and NaOAc (20.0 mmol) were added in propanoic acid (80 mL) and the mixture was heated and refluxed for 12 h. After removal of propanoic acid, the mixture was extracted three times using CH$_2$Cl$_2$ as extracting solvent and the extracted mixture was washed by deionized water, followed by removing the water in the solution by Na$_2$SO$_4$. The solvent was evaporated and the residue was purified by silica gel column chromatography, eluted with ethyl acetate and hexane (1:1) to obtain the bis-tridentate Ir(III) complex.

Data of the complex (1a-18): yellow solid; yield: 30%; $^1$H NMR (400 MHz, DMSO-d$_6$): δ 8.40 (t, J=7.6 Hz, 2H), 8.26 (t, J=7.6 Hz, 1H), 7.98 (dd, J=7.6, 1.2 Hz, 1H), 7.91 (s, 2H), 7.48~7.44 (m, 4H), 7.36~7.32 (m, 3H), 7.20 (s, 1H), 6.84 (dd, J=8.8, 5.2 Hz, 1H), 6.30~6.25 (m, 1H), 5.29 (dd, J=10.4, 3.2 Hz, 1H), 3.19 (s, 6H), 1.65 (s, 9H). $^{19}$F NMR (376 MHz, DMSO-d$_6$): δ −58.03 (s, 3F), −121.84 (s, 1F). FAB MS: m/z 907.3 (M+H$^+$).

Examples 18-19

Preparation of Complexes (1a-19) to (1a-20)

The functional bis(imidazolium) benzene chelate (1.0 mmol), [Ir(cod)(μ-Cl)]$_2$ (0.5 mmol) and NaOAc (5.0 mmol)

were added in CH₃CN (80 mL) and the mixture was heated and refluxed for 12 h. After removal of acetonitrile, the 2-phenyl-6-pyrazolyl-pyrimidine class of chelate (1.0 mmol) and xylene (80 mL) were added, and the mixture was heated and refluxed at 150° C. for another 12 h. The solvent was evaporated and the residue was purified by silica gel column chromatography, eluted with ethyl acetate and hexane (1:3) to obtain the bis-tridentate Ir(III) complexes.

Data of the complex (1a-19): orange-red solid; yield: 45%; $^1$H NMR (400 MHz, acetone-$d_6$): δ 8.89 (d, J=8.0 Hz, 1H), 8.26 (d, J=8.0 Hz, 1H), 8.18 (dd, J=8.0, 1.2 Hz, 1H), 8.06~8.02 (m, 3H), 7.89~7.85 (m, 1H), 7.80 (s, 1H), 7.63 (s, 2H), 7.09 (d, J=2.4 Hz, 2H), 6.83 (td, J=7.6, 1.2 Hz, 1H), 6.61 (td, J=7.6, 1.2 Hz, 1H), 5.96 (dd, J=7.6, 1.2 Hz, 1H), 3.19~3.12 (m, 2H), 1.54 (s, 9H), 0.68 (d, J=6.8 Hz, 6H), 0.60 (d, J=6.8 Hz, 6H). $^{19}$F NMR (376 MHz, acetone-$d_6$): δ −60.46 (s, 3F). FAB MS: m/z 880.4 (M+H⁺).

Data of the complex (1a-20): orange-red solid; yield: 32%; $^1$H NMR (400 MHz, acetone-$d_6$): δ 8.06 (dd, J=7.6, 1.2 Hz, 1H), 8.01 (d, J=2.0 Hz, 2H), 7.98 (s, 1H), 7.59 (s, 2H), 7.28 (s, 1H), 7.08 (d, J=2.0 Hz, 2H), 6.79 (td, J=7.6, 1.2 Hz, 1H), 6.57 (td, J=7.6, 1.2 Hz, 1H), 5.93 (dd, J=7.6, 1.2 Hz, 1H), 3.28~3.21 (m, 2H), 1.61 (s, 9H), 1.52 (s, 9H), 0.75 (d, J=6.8 Hz, 6H), 0.73 (d, J=6.8 Hz, 6H). $^{19}$F NMR (376 MHz, acetone-$d_6$): δ −60.44 (s, 3F). FAB MS: m/z 886.4 (M+H⁺).

Examples 20-23

Preparation of Complexes (1b-1), (1b-2), (1c-1) and (1c-2)

The functional bis(imidazolium) benzene chelate (1.0 mmol), [Ir(cod)(μ-Cl)]₂ (0.5 mmol) and NaOAc (5.0 mmol) were added in CH₃CN (80 mL) and the mixture was heated and refluxed for 12 h. After the solvent was removed under vacuum, the dianionic chelates, 2,6-bis(5-trifluoromethyl-pyrazol-3-yl) pyridine or 2,6-di(2,4-difluorophenyl)pyridine (1.0 mmol), and xylene (80 mL) were added. The mixture was heated and refluxed at 150° C. for another 12 h. The solvent was evaporated and the residue was purified by silica gel column chromatography, eluted with CH₂Cl₂ and ethyl acetate (20:1) or CH₂Cl₂ and hexane (1:3) to obtain the bis-tridentate Ir(III) complexes.

Data of the complex (1b-1): yellow solid; yield: 52%; $^1$H NMR (400 MHz, acetone-$d_6$): δ 8.16 (t, J=8.0 Hz, 1H), 8.06 (d, J=2.4 Hz, 2H), 7.97 (d, J=8.0 Hz, 2 H), 7.59 (s, 2H), 7.20 (d, J=2.4 Hz, 2H), 7.08 (s, 2H), 3.40~3.33 (m, 2H), 1.51 (s, 9H), 0.83 (d, J=6.8 Hz, 12H). $^{19}$F NMR (376 MHz, acetone-$d_6$): δ −60.50 (s, 6F). FAB MS: m/z 888.3 (M+H⁺). Anal. Calcd. for C₃₅H₃₄F₆IrN₉: C, 47.40; H, 3.86; N, 14.21. Found: C, 47.06; H, 3.86; N, 14.16.

Data of the complex (1b-2): yellow solid; yield: 72%; $^1$H NMR (400 MHz, acetone-$d_6$): δ 8.22 (d, J=2.4 Hz, 2H), 8.21 (t, J=8.0 Hz, 1H), 8.02 (d, J=8.0 Hz, 2H), 7.85 (s, 2H), 7.31 (d, J=2.4 Hz, 2H), 7.10 (s, 2H), 3.43~3.33 (m, 2H), 0.87 (d, J=6.8 Hz, 12H). $^{19}$F NMR (376 MHz, acetone-$d_6$): δ −60.65 (s, 3F), −60.69 (s, 6F). FAB MS: m/z 899.6 (M+H⁺). Anal. Calcd. for C₃₂H₂₅F₉IrN₉: C, 42.76; H, 2.80; N, 14.03. Found: C, 42.67; H, 2.80; N, 13.96.

Data of the complex (1c-1): yellow solid; yield: 5%; $^1$H NMR (400 MHz, acetone-$d_6$): δ 8.15 (d, J=8.0 Hz, 2H), 8.01 (d, J=2.4 Hz, 2H), 7.96 (t, J=8.0 Hz, 1H), 7.61 (s, 2H), 7.05 (d, J=2.4 Hz, 2H), 6.35~6.29 (m, 2H), 5.80 (dd, J=7.6, 2.4 Hz, 2H), 3.27~3.20 (m, 2H), 1.53 (s, 9H), 0.77 (d, J=6.8 Hz, 12H). $^{19}$F NMR (376 MHz, acetone-$d_6$): δ −113.09 (d, J=8.3 Hz, 2F), −113.34 (d, J=8.3 Hz, 2F). FAB MS: m/z 843.3 (M+H⁺).

Data of the complex (1c-2): yellow solid; yield: 14%; $^1$H NMR (400 MHz, acetone-$d_6$): δ 8.18 (d, J=8.0 Hz, 2H), 8.17 (d, J=2.4 Hz, 2H), 8.02 (t, J=8.0 Hz, 1H), 7.84 (s, 2H), 7.17 (d, J=2.4 Hz, 2H), 6.38~6.33 (m, 2H), 5.68 (dd, J=7.6, 2.4 Hz, 2H), 3.34~3.24 (m, 2H), 0.81 (d, J=6.8 Hz, 12H). $^{19}$F NMR (376 MHz, acetone-$d_6$): δ −59.82 (s, 3F), −112.60 (d, J=8.3 Hz, 2F), −112.80 (d, J=8.3 Hz, 2F). FAB MS: m/z 855.3 (M+H⁺).

Example 24

Preparation of Complex (1a-31)

The functional bis(imidazolium) benzene chelate (1.0 mmol), IrCl₃·3H₂O (1.0 mmol), 4-(tert-butyl)-2-(4-(tert-butyl)phenyl)-6-(3-(trifluoromethyl)-1H-pyrazol-5-yl) pyrimidine (1.0 mmol) and NaOAc (20.0 mmol) were added in propanoic acid (80 mL) and the mixture was heated and refluxed for 12 h. After removal of propanoic acid, the mixture was extracted three times using CH₂Cl₂ as extracting solvent and the extracted mixture was washed by deionized water, followed by removing the water in the solution by Na₂SO₄. The solvent was evaporated and the residue was purified by silica gel column chromatography, eluted with ethyl acetate and hexane (1:1) to obtain the bis-tridentate Ir(III) complex.

Data of the complex (1a-31): yellow solid; yield: 20%; $^1$H NMR (400 MHz, CDCl₃): δ 7.94 (d, J=8.0 Hz, 1H), 7.49 (s, 1H), 7.41 (d, J=2.0, 2H), 7.26 (s, 2H), 7.10 (s, 1H), 6.83 (dd, J=8.0, 2.0 Hz, 1H), 6.50 (d, J=2.0 Hz, 2H), 5.57 (d, J=2.0 Hz, 1H), 2.73 (s, 6H), 1.53 (s, 9H), 1.49 (s, 9H), 0.87 (s, 9H). $^{19}$F NMR (376 MHz, CDCl₃): δ −59.80 (s, 3F).

Example 25

Preparation of Complex (1a-32)

The functional bis(imidazolium) benzene chelate (1.0 mmol), IrCl₃·3H₂O (1.0 mmol), 2-(trifluoromethyl)-5-(6-(3-(trifluoromethyl)-1H-pyrazol-5-yl)pyridin-2-yl) pyrimidine (1.0 mmol) and NaOAc (20.0 mmol) were added in propanoic acid (80 mL) and the mixture was heated and refluxed for 12 h. After removal of propanoic acid, the mixture was extracted three times using CH₂Cl₂ as extracting solvent and the extracted mixture was washed by deionized water, followed by removing the water in the solution by Na₂SO₄. The solvent was evaporated and the residue was purified by silica gel column chromatography, eluted with ethyl acetate and hexane (1:1) to obtain the bis-tridentate Ir(III) complex.

Data of the complex (1a-32): yellow solid; yield: 37%; $^1$H NMR (400 MHz, acetone-$d_6$): δ 8.84 (s, 1H), 8.29 (dd, J=7.6, 1.2 Hz, 1H), 8.14 (t, J=7.6, 1H), 8.10 (dd, J=7.6, 1.2 Hz, 1H), 7.98 (d, J=2.0 Hz, 2H), 7.54 (s, 2H), 7.11 (s, 1H), 6.95 (d, J=2.0 Hz, 2H), 2.88 (s, 6H), 1.50 (s, 9H). $^{19}$F NMR (376 MHz, acetone-$d_6$): δ −60.25 (s, 3F), −70.45 (s, 3F).

Example 26

Preparation of Complex (1a-33)

The functional bis(imidazolium) benzene chelate (1.0 mmol), [Ir(cod)(μ-Cl)]₂ (0.5 mmol) and NaOAc (5.0 mmol) were added in CH₃CN (80 mL) and the mixture was heated and refluxed for 12 h. After removal of acetonitrile, the 1-phenyl-3-(3-(trifluoromethyl)-1H-pyrazol-5-yl) isoquinoline (1.0 mmol) and xylene (80 mL) were added, and the mixture was heated and refluxed at 150° C. for another 12 h. The xylene was then replaced with decalin (80 mL) and the mixture was heated and refluxed for another 48 h. The solvent was evaporated and the residue was purified by silica gel column chromatography, eluted with $CH_2Cl_2$ and ethyl acetate (10:1) to obtain the bis-tridentate Ir(III) complex.

Data of the complex (1a-33): red solid; yield: 27%; $^1H$ NMR (400 MHz, acetone-$d_6$): δ 9.10~9.07 (m, 1H), 8.44 (d, J=8.0 Hz, 1H), 8.35 (s, 1H), 8.20~8.18 (m, 1H), 7.96 (d, J=2.0, 2H), 7.18~7.77 (m, 2H), 7.60 (m, 2H), 7.07 (s, 1H), 6.96~6.87 (m, 1H), 6.87 (d, J=2.0, 2H), 6.54 (td, J=7.6, 1.2 Hz, 1H), 6.09 (dd, J=7.6, 1.2 Hz, 1H), 2.73 (s, 6H), 1.53 (s, 9H). $^{19}F$ NMR (376 MHz, acetone-$d_6$): δ −60.00 (s, 3F).

Figure 2:
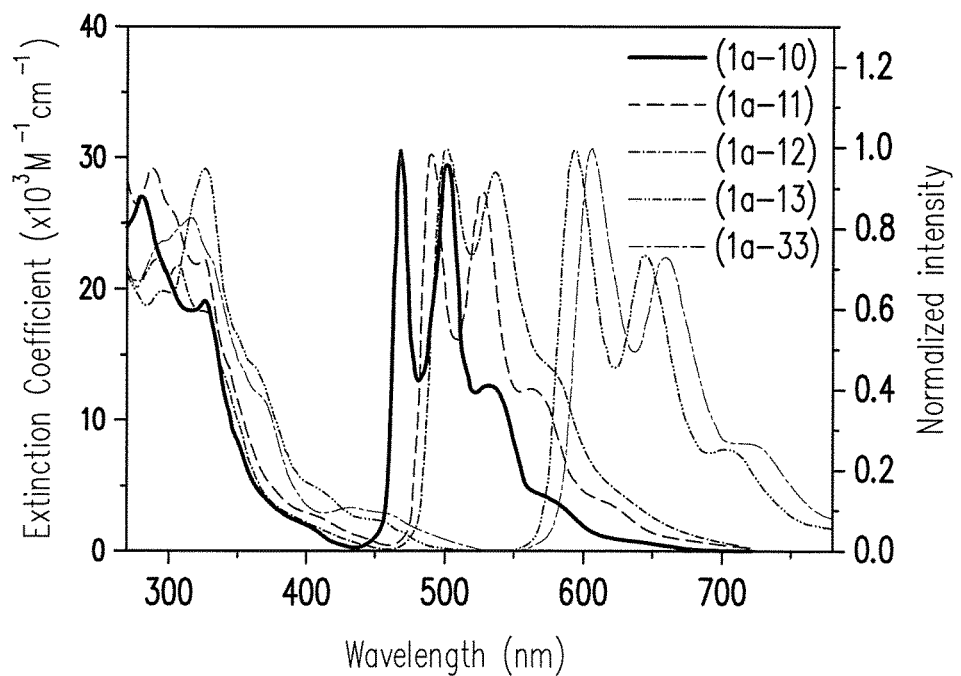
FIG. 2 shows the absorption spectra and the phosphorescence spectra of the iridium complexes (1a-10) to (1a-13) and (1a-33) of the invention.

The absorption spectra and the phosphorescence spectra of the iridium complexes (1a-10) to (1a-13) and (1a-33) that were synthesized in Examples 10 to 13 and 26 are shown in FIG. 2, and the maximum emission peak location ($\lambda_{em}$), the quantum yield (φ)), and the phosphorescence lifetime (τ) thereof are listed in Table 3 below.

TABLE 3

| Complex | $\lambda_{max}$/nm$^a$ | φ (%)$^{a, b}$ | $\tau_{obs}$/µs$^a$ |
|---|---|---|---|
| (1a-10) | 467, 501, 532, 583 | 99 | 5.41 |
| (1a-11) | 490, 526, 566, 618 | 92 | 4.65 |
| (1a-12) | 501, 535, 582, 632 | 100 | 2.84 |
| (1a-13) | 593, 643, 702 | 100 | 8.20 |
| (1a-33) | 605, 659, 726 | 80 | 4.65 |

$^a$Measured in degassed $CH_2Cl_2$ solution.
$^b$Coumarin 480 ($\lambda_{max}$ = 480 nm, Φ~0.80 in MeOH), coumarin 153 ($\lambda_{max}$ = 530 nm, Φ~0.58 in EtOH) and DCM ($\lambda_{max}$ = 637 nm, Φ~0.80 in DMSO) were used as standard.

It is clear from FIG. 2 and Table 3 that the iridium complexes (1a-10) to (1a-13) and (1a-33) have high quantum yields, and the iridium complexes (1a-13) and (1a-33) in which the left tridentate chelate N^N^C further includes a benzo-ring can enhance conjugation of the chromophore to reduce the energy gap and make a red shift of the emitted light.

Figure 3:
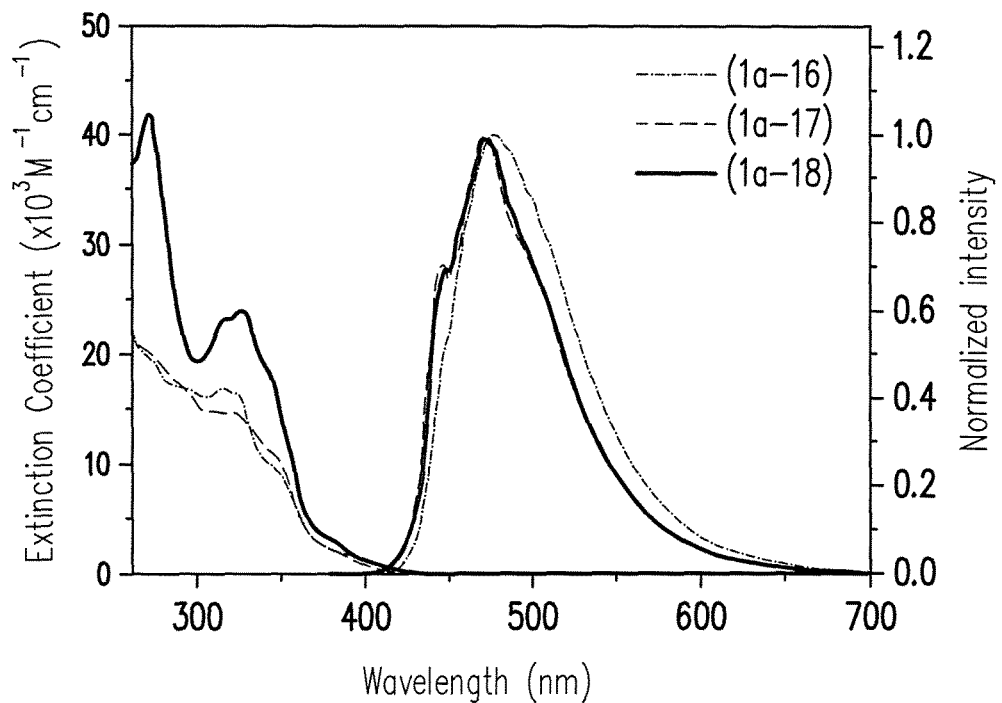
FIG. 3 shows the absorption spectra and the phosphorescence spectra of the iridium complexes (1a-16), (1a-17) and (1a-18) of the invention.

The absorption spectra and the phosphorescence spectra of the iridium complexes (1a-16), (1a-17) and (1a-18) that were synthesized in Examples 15, 16 and 17 are shown in FIG. 3, and the maximum emission peak location ($\lambda_{em}$), the quantum yield (φ), and the phosphorescence lifetime (τ) thereof are listed in Table 4 below.

TABLE 4

| Complex | $\lambda_{max}$/nm$^a$ | φ (%)$^{a, b}$ | $\tau_{obs}$/µs$^a$ |
|---|---|---|---|
| (1a-16) | 478 | 82 | 4.42 |
| (1a-17) | 447, 471, 505 | 81 | 25.11 |
| (1a-18) | 448, 473, 506 | 79 | 18.63 |

$^a$Measured in degassed $CH_2Cl_2$ solution.
$^b$Coumarin 480 ($\lambda_{max}$ = 480 nm, Φ~0.80 in MeOH) was used as standard.

It is clear from FIG. 3 and Table 4 that the iridium complexes (1a-16), (1a-17) and (1a-18) have high quantum yields, and the left tridentate chelates N^N^C are non-conjugated so as to make a blue shift of the emitted light.

Other effects of the above complexes are described below. As compared to the N—Ir bonding formed by coordination of a pyridine ligand to iridium, the C—Ir bonding formed by coordination of carbene as a strong-field ligand to iridium is stronger, so that the stability of the complex is higher. Regarding the luminous performance, the strong coordination bonding can raise the transition energy to the metal-centered dd excited states and to reduce the non-radiative quenching of phosphorescence, thus improving the luminous efficiency and the color purity. In addition, as compared to the conventional tris-bidentate iridium complexes, the bis-tridentate iridium complex of the invention has higher rigidity, and therefore improves the luminous efficiency and the device stability.

Example 27

Fabrication of an OLED

Figure 4:
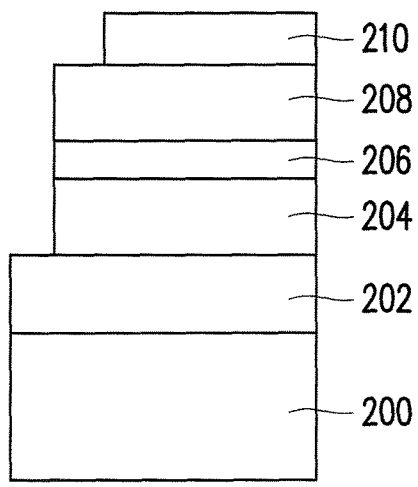
FIG. 4 illustrates a schematic OLED structure including an iridium complex of the invention.

An OLED was fabricated using the one of above complexes. The structure thereof was schematically illustrated in FIG. 4, including a glass substrate 200, an anode 202, a hole transportation layer 204, a light-emitting layer 206, an electron transportation layer 208 and a cathode 210. The material of the anode 202 is ITO. The material of the hole transportation layer 204 is TAPC. The material of the light-emitting layer 206 is mCP doped with one of the iridium complexes of the invention. The material of the electron transportation layer 208 is TmPyPB. The material of the cathode 210 is LiF/Al.

As mentioned above, the iridium complex of the invention has strong coordination bonding so that the transition energy to the metal-centered dd excited states is raised and the non-radiative of phosphorescence is reduced, thus improving the luminous efficiency and the color purity. In addition, the iridium complex of the invention includes a pincer carbene chelate as a strong-field ligand, which form stronger bonding with iridium so that the stability of the complex is higher.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. An iridium complex, being represented by formula (1):

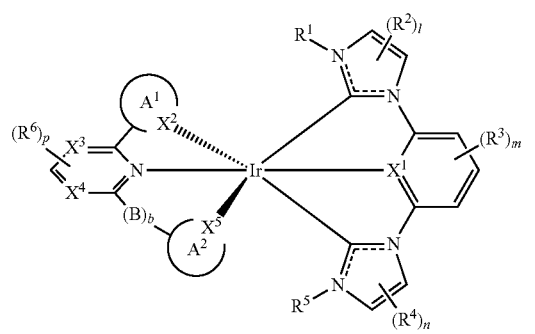

(1)

wherein
each of l and n is an integer of 1 to 2;
each of m and p is an integer of 1 to 3;
b is an integer of 0 or 1;
$R^1$ is substituted or unsubstituted $C_{1-12}$ alkyl;

each of $R^2$'s is independently hydrogen or substituted or unsubstituted $C_{1-12}$ alkyl, provided that when l=2, two $R^2$'s may join to form a $C_{3-8}$ N-heteroaromatic or aromatic ring;

each of $R^3$'s is independently hydrogen, fluorine or —$C_xF_{2x+1}$ (x=1, 2 or 3), substituted or unsubstituted $C_{1-12}$ alkyl, or substituted or unsubstituted $C_{6-12}$ aryl, provided that when m≥2, two or more $R^3$'s may join to form a $C_{3-8}$ aromatic ring;

each of $R^4$'s is independently hydrogen or substituted or unsubstituted $C_{1-12}$ alkyl, provided that when n=2, two $R^4$'s may join to form a $C_{3-8}$ N-heteroaromatic or aromatic ring;

$R^5$ is substituted or unsubstituted $C_{1-12}$ alkyl;

each of $R^6$'s is independently hydrogen, fluorine or —$C_xF_{2x+1}$ (x=1, 2 or 3), substituted or unsubstituted $C_{1-12}$ alkyl, or substituted or unsubstituted $C_{6-12}$ aryl, provided that when p≥2, two or more $R^6$'s may join to form a $C_{3-8}$ N-heteroaromatic or aromatic ring;

each of $X^1$, $X^2$, $X^3$, $X^4$ and $X^5$ is independently nitrogen or carbon;

each of $A^1$ and $A^2$ is independently a 5-membered or 6-membered unsaturated ring containing 0, 1, 2, 3 or 4 nitrogen atoms and 0 oxygen or sulphur atom; and B is —O—, —$CH_2$—, —$CR_2$— or —NR— (R=methyl, ethyl or propyl), provided that when b=1.

2. The iridium complex of claim 1, wherein $A^1$ is a 5-membered ring and $A^2$ is a 6-membered ring, the iridium complex being represented by formula (1a):

(1a)

wherein q is an integer of 1 to 2;

r is an integer of 1 to 4;

each of $R^7$'s is independently hydrogen, fluorinated alkyl —$C_xF_{2x+1}$ (x=1, 2 or 3) or substituted or unsubstituted $C_{1-12}$ alkyl;

each of $R^8$'s is independently hydrogen, fluorinated alkyl —$C_xF_{2x+1}$ (x=1, 2 or 3) or substituted or unsubstituted $C_{1-12}$ alkyl, provided that when r≥2, two or more $R^7$'s may join to form a $C_{3-8}$ N-heteroaromatic or aromatic ring;

each of $X^6$, $X^7$, $X^8$, $X^9$ and $X^{10}$ is independently nitrogen or carbon; and l, m, n, p, b, $R^1$-$R^6$, $X^1$-$X^5$, $A^1$, $A^2$ and B are defined as in claim 1.

3. The iridium complex of claim 2, having a structure selected from one of formulae (1a-1) to (1a-33):

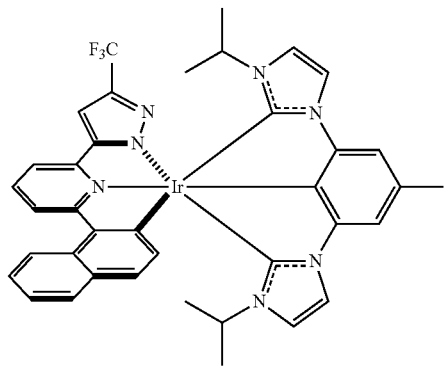

1a-1

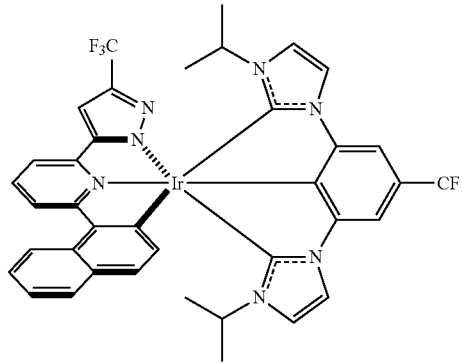

1a-2

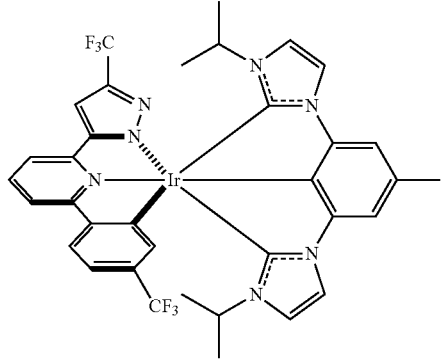

1a-3

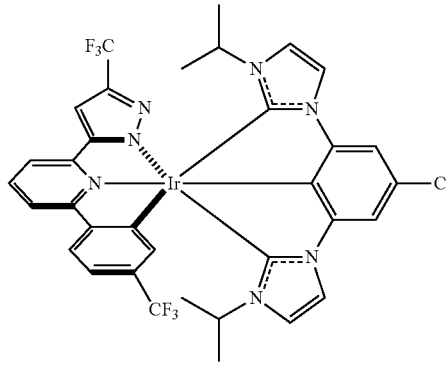

1a-4

1a-5
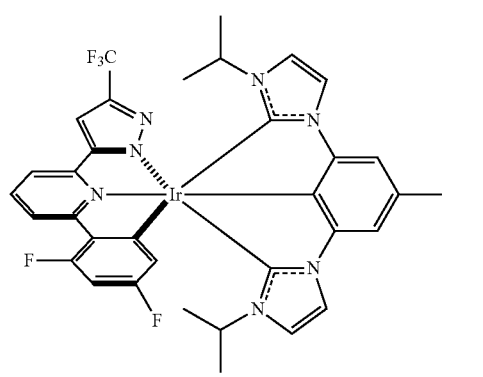
1a-6
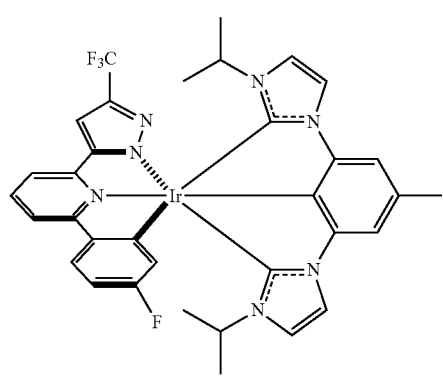
1a-7
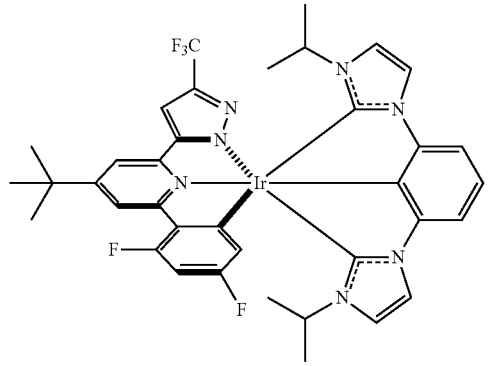
1a-8
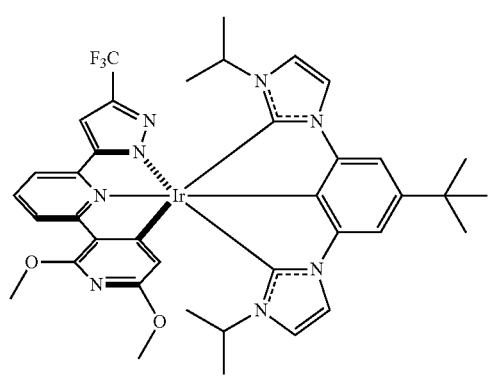
1a-9
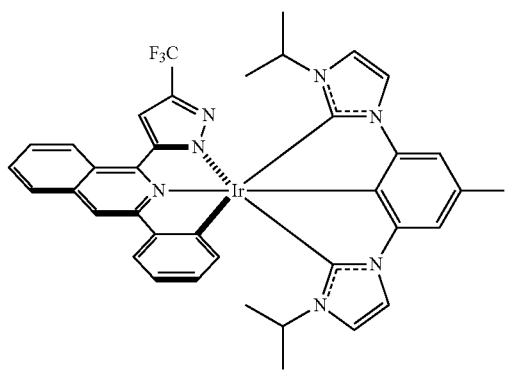
1a-10
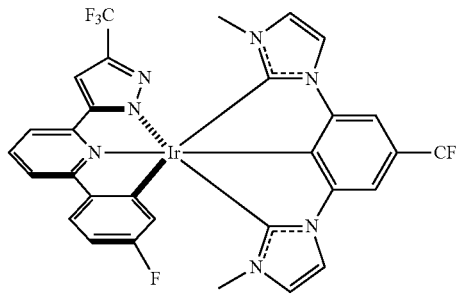
1a-11
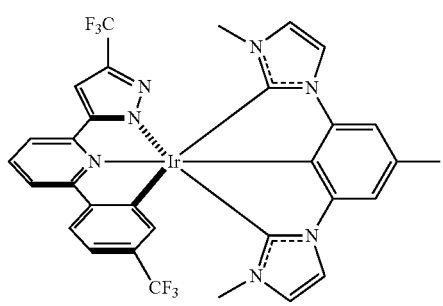
1a-12
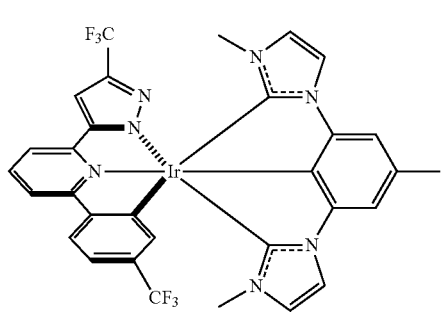
1a-13
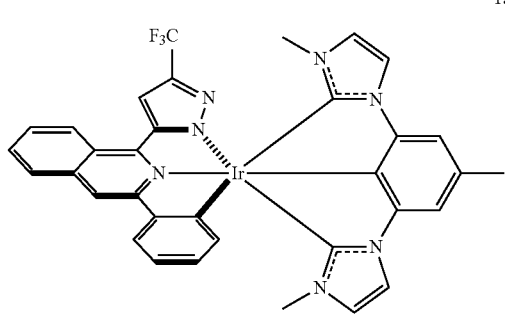

-continued
1a-14
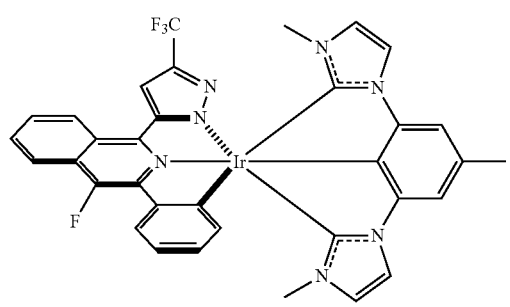
1a-15
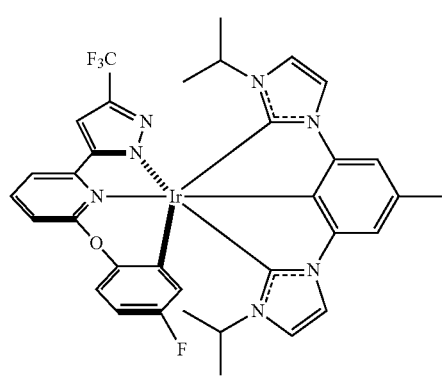
1a-16
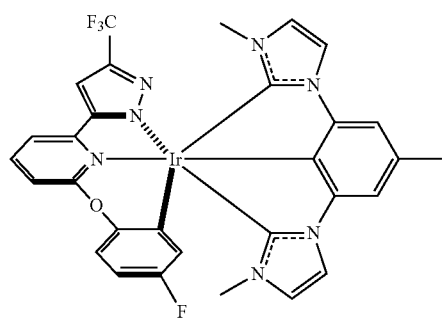
1a-17
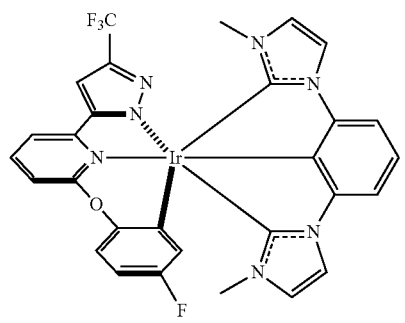
-continued
1a-18
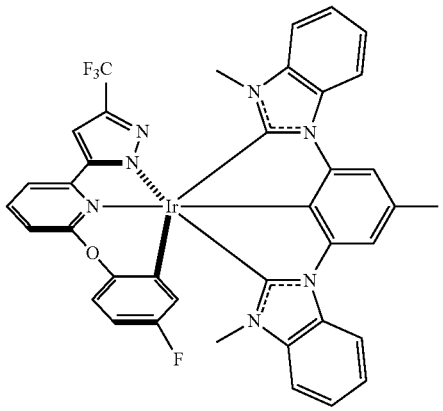
1a-19
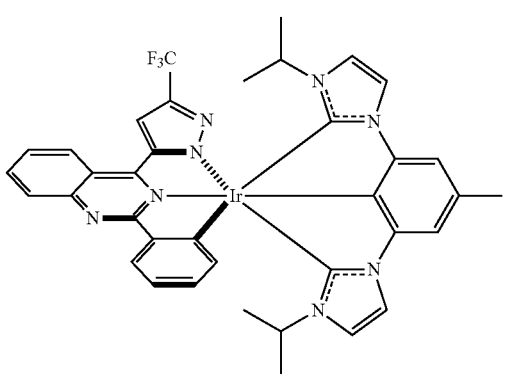
1a-20
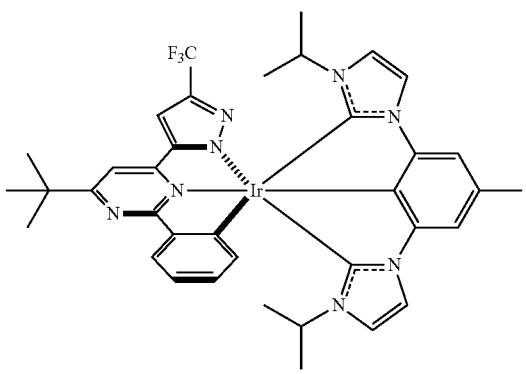
1a-21
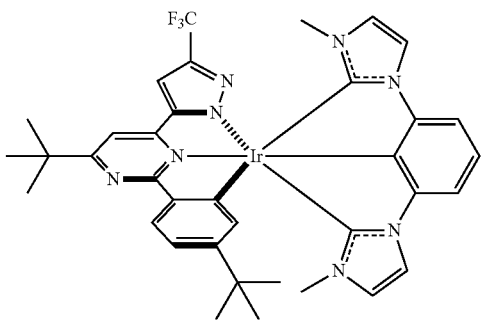

1a-22
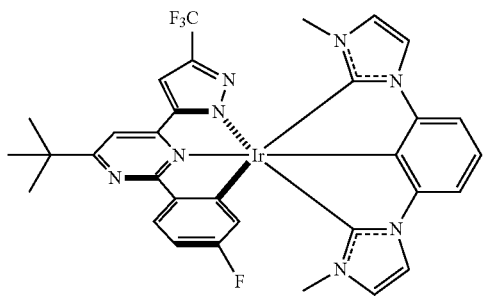
1a-23
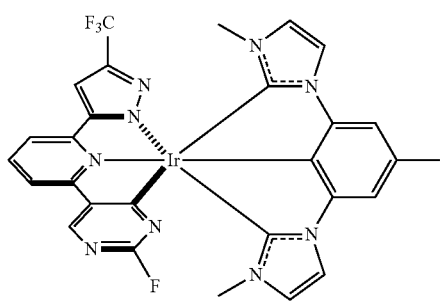
1a-24
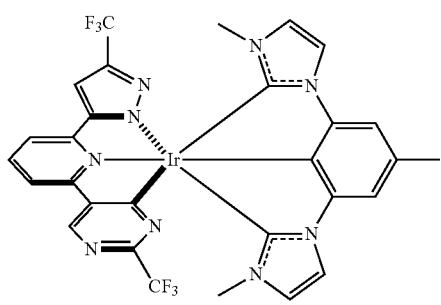
1a-25
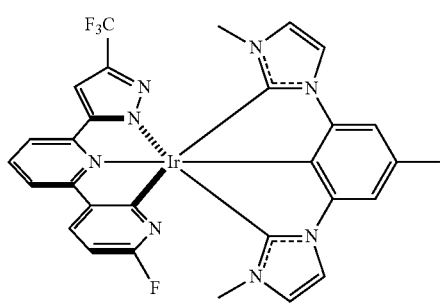
1a-26
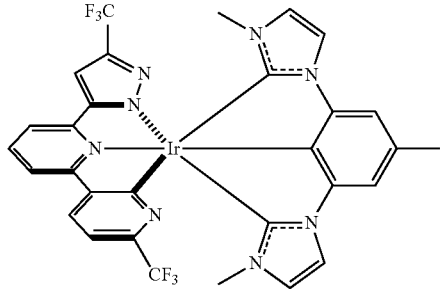
1a-27
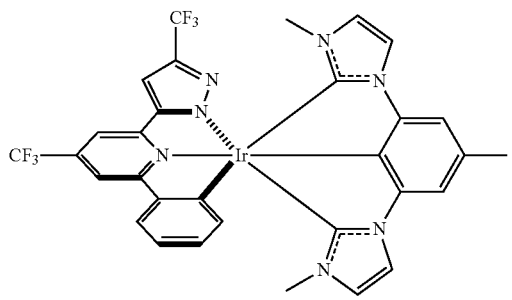
1a-28
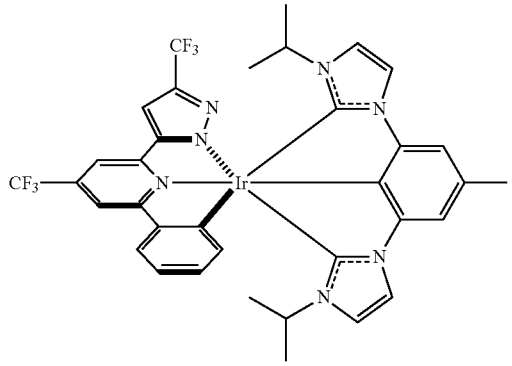
1a-29
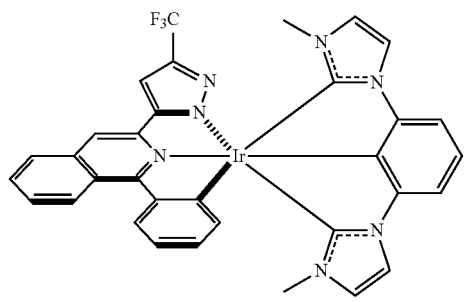
1a-30
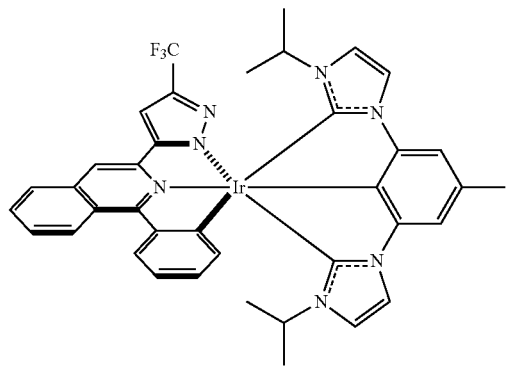

-continued

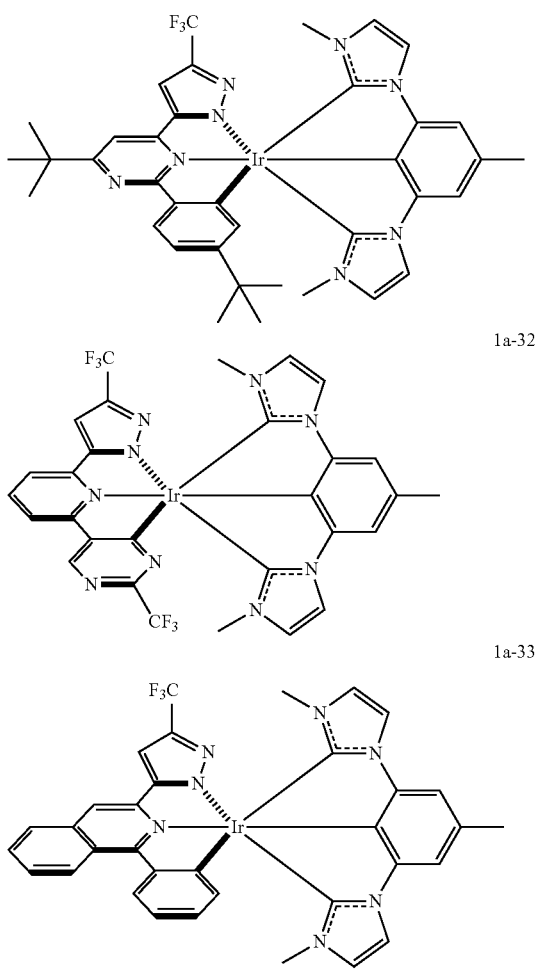

1a-31

1a-32

1a-33

4. The iridium complex of claim 1, wherein $A^1$ is a 5-membered ring and $A^2$ is a 5-membered ring, the iridium complex being represented by formula (1b):

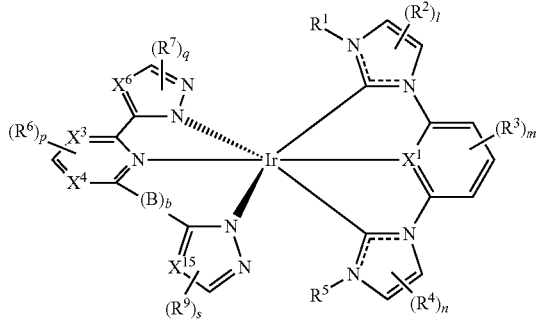

(1b)

wherein
each of q and s is an integer of 1 to 2;
each of $R^7$'s is independently hydrogen, fluorinated alkyl —$C_xF_{2x+1}$ (x=1, 2 or 3) or substituted or unsubstituted $C_{1-12}$ alkyl;
each of $R^9$'s is independently hydrogen, fluorinated alkyl —$C_xF_{2x+1}$ (x=1, 2 or 3) or substituted or unsubstituted $C_{1-12}$ alkyl;
each of $X^6$ and $X^{15}$ is nitrogen or carbon; and l, m, n, p, b, $R^1$-$R^6$, $X^1$-$X^5$, $A^1$, $A^2$ and B are defined as in claim 1.

5. The iridium complex of claim 4, having a structure selected from one of formulae (1b-1) to (1b-2):

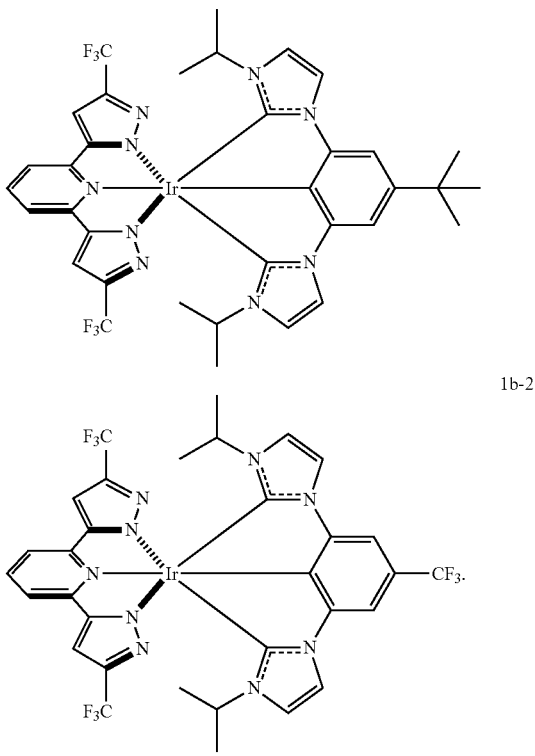

1b-1

1b-2

6. The iridium complex of claim 1, wherein $A^1$ is a 6-membered ring and $A^2$ is a 6-membered ring, the iridium complex being represented by formula (1c):

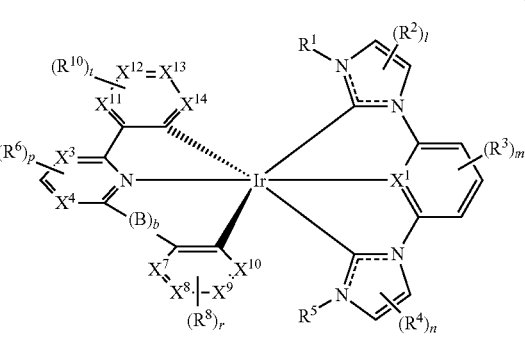

(1c)

wherein
each of t and r is an integer of 1 to 4;
each of $R^8$'s is independently hydrogen, fluorinated alkyl —$C_xF_{2x+1}$ (x=1, 2 or 3) or substituted or unsubstituted $C_{1-12}$ alkyl, provided that when r≥2, two or more $R^8$'s may join to form a $C_{3-8}$ aromatic ring;
each of $R^{10}$'s is independently hydrogen, fluorinated alkyl —$C_xF_{2x+1}$ (x=1, 2 or 3) or substituted or unsubstituted $C_{1-12}$ alkyl, provided that when t≥2, two or more $R^{10}$'s may join to form a $C_{3-8}$ aromatic ring;
each of $X^7$, $X^8$, $X^9$, $X^{10}$, $X^{11}$, $X^{12}$, $X^{13}$ and $X^{14}$ is independently nitrogen or carbon; and
l, m, n, p, b, $R^1$-$R^6$, $X^1$-$X^5$, $A^1$, $A^2$ and B are defined as in claim 1.

7. The iridium complex of claim 6, having a structure selected from one of formulae (1c-1) to (1c-2):

1c-1

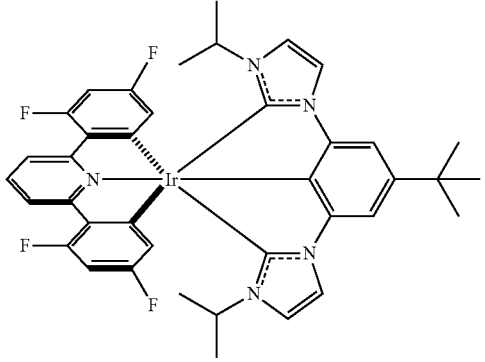

1c-2

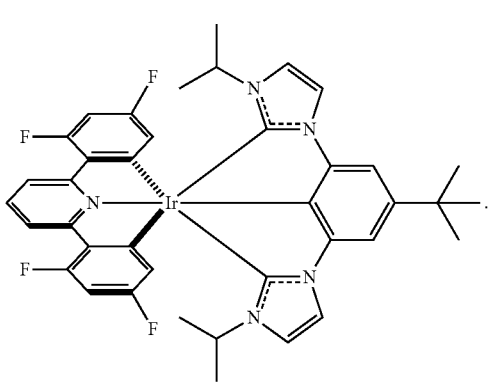

8. An organic light-emitting diode, comprising two electrodes and a light-emitting layer disposed between the two electrodes, wherein the light-emitting layer contains the iridium complex of claim 1.

9. The organic light-emitting diode of claim 8, wherein the iridium complex functions as a dopant in a host material of the light-emitting layer.

10. An organic light-emitting diode, comprising two electrodes and a light-emitting layer disposed between the two electrodes, wherein the light-emitting layer contains the iridium complex of claim 2.

11. The organic light-emitting diode of claim 10, wherein the iridium complex functions as a dopant in a host material of the light-emitting layer.

12. An organic light-emitting diode, comprising two electrodes and a light-emitting layer disposed between the two electrodes, wherein the light-emitting layer contains the iridium complex of claim 4.

13. The organic light-emitting diode of claim 12, wherein the iridium complex functions as a dopant in a host material of the light-emitting layer.

14. An organic light-emitting diode, comprising two electrodes and a light-emitting layer disposed between the two electrodes, wherein the light-emitting layer contains the iridium complex of claim 6.

15. The organic light-emitting diode of claim 14, wherein the iridium complex functions as a dopant in a host material of the light-emitting layer.

* * * * *